United States Patent
Funk et al.

(10) Patent No.: US 12,194,250 B2
(45) Date of Patent: Jan. 14, 2025

(54) SYSTEMS AND METHODS FOR CONTROLLING CATHETER DEVICE SIZE

(71) Applicant: Velano Vascular, Inc., San Francisco, CA (US)

(72) Inventors: Brian J. Funk, San Francisco, CA (US); Kevin J. Ehrenreich, San Francisco, CA (US)

(73) Assignee: Velano Vascular, Inc., San Francisco, CA (US)

( * ) Notice: Subject to any disclaimer, the term of this patent is extended or adjusted under 35 U.S.C. 154(b) by 0 days.

(21) Appl. No.: 18/221,123

(22) Filed: Jul. 12, 2023

(65) Prior Publication Data

US 2023/0355926 A1   Nov. 9, 2023

Related U.S. Application Data

(63) Continuation of application No. 17/735,610, filed on May 3, 2022, now Pat. No. 11,744,990, which is a
(Continued)

(51) Int. Cl.
*A61M 25/01* (2006.01)
*A61B 5/15* (2006.01)
(Continued)

(52) U.S. Cl.
CPC ..... *A61M 25/0113* (2013.01); *A61B 5/15003* (2013.01); *A61B 5/150992* (2013.01);
(Continued)

(58) Field of Classification Search
CPC .......... A61M 25/0113; A61M 25/0023; A61M 25/0136; A61M 2025/0004;
(Continued)

(56) References Cited

U.S. PATENT DOCUMENTS

| | | |
|---|---|---|
| 3,262,448 A | 7/1966 | Ring et al. |
| 3,766,913 A | 10/1973 | Moorehead et al. |

(Continued)

FOREIGN PATENT DOCUMENTS

| | | |
|---|---|---|
| CN | 101884823 A | 11/2010 |
| EP | 1191970 B1 | 3/2006 |

(Continued)

OTHER PUBLICATIONS

Office Action for U.S. Appl. No. 13/234,857, mailed Apr. 16, 2015, 17 pages.
Office Action for U.S. Appl. No. 13/456,900, mailed Sep. 5, 2012, 11 pages.
Office Action for U.S. Appl. No. 13/456,900, mailed Nov. 2, 2012, 6 pages.
(Continued)

*Primary Examiner* — Michael J Tsai
*Assistant Examiner* — Rachel T. Smith
(74) *Attorney, Agent, or Firm* — The Webb Law Firm

(57) ABSTRACT

An apparatus includes a catheter, a housing configured to house at least a portion of the catheter, and an actuator movably coupled to the housing. The housing has a first port configured to receive a proximal end portion of the catheter and a second port configured to couple the housing to an indwelling vascular access device. A portion of the actuator is disposed within the housing and is configured to be movably coupled to a portion of the catheter. The actuator is configured to be moved a first distance to move a distal end portion of the catheter a second distance greater than the first distance from a first position to a second position. The distal end portion of the catheter is disposed within the housing when in the first position and is distal to the indwelling vascular access device when in the second position.

8 Claims, 4 Drawing Sheets

Related U.S. Application Data continuation of application No. 17/019,763, filed on Sep. 14, 2020, now Pat. No. 11,351,340, which is a continuation of application No. 15/927,506, filed on Mar. 21, 2018, now Pat. No. 10,773,056.

(60) Provisional application No. 62/474,203, filed on Mar. 21, 2017.

(51) Int. Cl.
    *A61M 25/00* (2006.01)
    *A61M 25/06* (2006.01)

(52) U.S. Cl.
    CPC .............. *A61M 2025/0004* (2013.01); *A61M 25/0023* (2013.01); *A61M 25/0136* (2013.01); *A61M 2025/0681* (2013.01)

(58) Field of Classification Search
    CPC ............ A61M 2025/0681; A61M 2025/0006; A61B 5/15003; A61B 5/150992; A61B 2017/3443
    See application file for complete search history.

(56) References Cited

U.S. PATENT DOCUMENTS

| | | |
|---|---|---|
| 4,068,659 A | 1/1978 | Moorehead |
| 4,192,319 A | 3/1980 | Hargens et al. |
| 4,314,555 A | 2/1982 | Sagae |
| 4,705,511 A | 11/1987 | Kocak |
| 4,790,830 A | 12/1988 | Hamacher |
| 4,808,158 A | 2/1989 | Kreuzer et al. |
| 4,808,165 A | 2/1989 | Carr |
| 4,935,010 A | 6/1990 | Cox et al. |
| 4,976,697 A | 12/1990 | Walder et al. |
| 5,013,304 A | 5/1991 | Russell et al. |
| 5,057,092 A | 10/1991 | Webster, Jr. |
| 5,069,674 A | 12/1991 | Fearnot et al. |
| 5,100,390 A | 3/1992 | Lubeck et al. |
| 5,135,502 A | 8/1992 | Koenig, Jr. et al. |
| 5,147,334 A | 9/1992 | Moss |
| 5,201,722 A | 4/1993 | Moorehead et al. |
| 5,203,771 A | 4/1993 | Melker et al. |
| 5,270,003 A | 12/1993 | Bernes et al. |
| 5,360,407 A | 11/1994 | Leonard |
| 5,368,029 A | 11/1994 | Holcombe et al. |
| 5,405,323 A | 4/1995 | Rogers et al. |
| 5,415,636 A | 5/1995 | Forman |
| 5,552,118 A | 9/1996 | Mayer |
| 5,553,625 A | 9/1996 | Rao |
| 5,562,631 A | 10/1996 | Bogert |
| 5,611,782 A | 3/1997 | Haedt |
| 5,658,263 A | 8/1997 | Dang et al. |
| 5,704,914 A | 1/1998 | Stocking et al. |
| 5,713,876 A | 2/1998 | Bogert et al. |
| 5,749,857 A | 5/1998 | Cuppy |
| 5,755,709 A | 5/1998 | Cuppy |
| 5,807,350 A | 9/1998 | Diaz |
| 5,827,229 A | 10/1998 | Auth et al. |
| 5,848,996 A | 12/1998 | Eldor |
| 5,853,393 A | 12/1998 | Bogert |
| 5,897,537 A | 4/1999 | Berg et al. |
| 5,911,715 A | 6/1999 | Berg et al. |
| 5,944,690 A | 8/1999 | Falwell et al. |
| 5,944,695 A | 8/1999 | Johnson et al. |
| 6,036,677 A | 3/2000 | Javier et al. |
| 6,059,759 A | 5/2000 | Mottola et al. |
| 6,080,138 A | 6/2000 | Lemke et al. |
| 6,093,177 A | 7/2000 | Javier et al. |
| 6,126,618 A | 10/2000 | Bischof |
| 6,197,001 B1 | 3/2001 | Wilson et al. |
| 6,394,979 B1 | 5/2002 | Forman et al. |
| 6,508,790 B1 | 1/2003 | Lawrence |
| 6,585,703 B1 | 7/2003 | Kassel et al. |
| 6,648,835 B1 | 11/2003 | Shemesh |
| 6,652,507 B2 | 11/2003 | Pepin |
| 6,685,664 B2 | 2/2004 | Levin et al. |
| 6,692,473 B2 | 2/2004 | St Cyr et al. |
| 6,712,790 B1 | 3/2004 | Prestidge et al. |
| 6,719,726 B2 | 4/2004 | Meng et al. |
| 6,719,781 B1 | 4/2004 | Kim |
| 6,722,370 B1 | 4/2004 | Mann |
| 6,755,812 B2 | 6/2004 | Peterson et al. |
| 6,858,024 B1 | 2/2005 | Berg et al. |
| 6,872,193 B2 | 3/2005 | Shaw et al. |
| 6,908,459 B2 | 6/2005 | Harding et al. |
| 6,913,595 B2 | 7/2005 | Mastorakis |
| 7,008,404 B2 | 3/2006 | Nakajima |
| 7,087,047 B2 | 8/2006 | Kraus et al. |
| 7,135,008 B2 | 11/2006 | O'Mahony et al. |
| 7,252,654 B2 | 8/2007 | VanTassel et al. |
| 7,311,689 B2 | 12/2007 | Levin et al. |
| 7,316,678 B2 | 1/2008 | Nash et al. |
| 7,462,161 B2 | 12/2008 | O'Mahony et al. |
| 7,615,033 B2 | 11/2009 | Leong |
| 7,625,367 B2 | 12/2009 | Adams et al. |
| 7,662,110 B2 | 2/2010 | Flaherty |
| 7,670,320 B2 | 3/2010 | Iwase et al. |
| 7,685,367 B2 | 3/2010 | Ruia et al. |
| 7,691,088 B2 | 4/2010 | Howell |
| 7,713,250 B2 | 5/2010 | Harding et al. |
| 7,717,882 B2 | 5/2010 | Harding |
| 7,717,899 B2 | 5/2010 | Bowe et al. |
| 7,762,977 B2 | 7/2010 | Porter et al. |
| 7,766,961 B2 | 8/2010 | Patel et al. |
| 7,771,394 B2 | 8/2010 | Shue et al. |
| 7,892,208 B2 | 2/2011 | Schnell et al. |
| 7,972,294 B2 | 7/2011 | Nash et al. |
| 8,048,031 B2 | 11/2011 | Shaw et al. |
| 8,062,226 B2 | 11/2011 | Moore |
| 8,092,374 B2 | 1/2012 | Smith et al. |
| 8,104,475 B2 | 1/2012 | Cheung |
| 8,162,890 B2 | 4/2012 | Amisar et al. |
| 8,211,089 B2 | 7/2012 | Winsor et al. |
| 8,251,978 B2 | 8/2012 | Nash et al. |
| 8,267,911 B2 | 9/2012 | Gallogly et al. |
| 8,328,759 B2 | 12/2012 | Donawick |
| 8,361,013 B2 | 1/2013 | Wood |
| 8,361,014 B2 | 1/2013 | Wood |
| 8,366,685 B2 | 2/2013 | Devgon |
| 8,372,032 B2 | 2/2013 | Wood |
| 8,425,532 B2 | 4/2013 | Flom et al. |
| 8,444,605 B2 | 5/2013 | Kuracina et al. |
| 8,491,568 B2 | 7/2013 | Schertiger et al. |
| 8,506,533 B2 | 8/2013 | Carlyon et al. |
| 8,523,801 B2 | 9/2013 | Nash et al. |
| 8,532,730 B2 | 9/2013 | Brister et al. |
| 8,690,833 B2 | 4/2014 | Belson |
| 8,696,639 B2 | 4/2014 | Smith et al. |
| 8,702,658 B2 | 4/2014 | Spearman |
| 8,721,546 B2 | 5/2014 | Belson |
| 8,728,035 B2 | 5/2014 | Warring et al. |
| 8,728,038 B2 | 5/2014 | Spearman |
| 8,728,058 B2 | 5/2014 | Schertiger |
| 8,753,312 B2 | 6/2014 | Bowe et al. |
| 8,808,246 B2 | 8/2014 | Cabot |
| 8,876,773 B2 | 11/2014 | Ishida |
| 8,932,259 B2 | 1/2015 | Stout et al. |
| 8,936,581 B2 | 1/2015 | Bihlmaier |
| 8,974,411 B2 | 3/2015 | Mckinnon |
| 9,028,425 B2 | 5/2015 | Burkholz |
| 9,056,182 B2 | 6/2015 | Moulton et al. |
| 9,084,851 B2 | 7/2015 | Kosinski et al. |
| 9,089,474 B2 | 7/2015 | Cederschiöld |
| 9,101,746 B2 | 8/2015 | Stout et al. |
| 9,114,241 B2 | 8/2015 | Stout et al. |
| 9,126,012 B2 | 9/2015 | McKinnon et al. |
| 9,149,604 B2 | 10/2015 | Nishide et al. |
| 9,155,876 B2 | 10/2015 | Sonderegger et al. |
| 9,186,100 B2 | 11/2015 | Devgon |
| 9,198,610 B2 | 12/2015 | Davis et al. |
| 9,220,871 B2 | 12/2015 | Thörne et al. |
| 9,233,208 B2 | 1/2016 | Tekeste |

(56) References Cited

U.S. PATENT DOCUMENTS

| | | |
|---|---|---|
| 9,302,049 B2 | 4/2016 | Tekeste |
| 9,314,201 B2 | 4/2016 | Burkholz et al. |
| 9,352,119 B2 | 5/2016 | Burkholz et al. |
| 9,352,128 B2 | 5/2016 | Ishida |
| 9,358,335 B2 | 6/2016 | Wada et al. |
| 9,381,320 B2 | 7/2016 | Vincent et al. |
| 9,399,112 B2 | 7/2016 | Shevgoor et al. |
| 9,402,975 B2 | 8/2016 | Shevgoor |
| 9,408,569 B2 | 8/2016 | Andreae et al. |
| 9,415,185 B2 | 8/2016 | Notter |
| 9,480,794 B2 | 11/2016 | Keith et al. |
| 9,522,229 B2 | 12/2016 | Sonderegger et al. |
| 9,522,237 B2 | 12/2016 | Alheidt et al. |
| 9,549,701 B2 | 1/2017 | Peterson et al. |
| 9,579,486 B2 | 2/2017 | Burkholz et al. |
| 9,592,374 B2 | 3/2017 | Muse |
| 9,616,214 B2 | 4/2017 | Stout et al. |
| 9,636,278 B2 | 5/2017 | Sanders et al. |
| 9,737,686 B2 | 8/2017 | Trainer et al. |
| 9,744,344 B1 | 8/2017 | Devgon et al. |
| 9,750,446 B2 | 9/2017 | Devgon et al. |
| 9,750,920 B2 | 9/2017 | Vincent et al. |
| 9,750,927 B2 | 9/2017 | Ma |
| 9,750,928 B2 | 9/2017 | Burkholz et al. |
| 9,770,580 B2 | 9/2017 | Burkholz et al. |
| 9,775,972 B2 | 10/2017 | Christensen et al. |
| 9,789,279 B2 | 10/2017 | Burkholz et al. |
| 9,839,385 B2 | 12/2017 | Burkholz |
| 9,895,092 B2 | 2/2018 | Burkholz |
| 9,907,913 B2 | 3/2018 | Kosinski et al. |
| 9,909,162 B2 | 3/2018 | Yeh |
| 9,919,826 B2 | 3/2018 | Ivosevic et al. |
| 9,943,676 B2 | 4/2018 | Tekeste |
| 9,980,878 B2 | 5/2018 | Marici et al. |
| 9,993,634 B2 | 6/2018 | Christensen et al. |
| 10,010,685 B2 | 7/2018 | Ferreri et al. |
| 10,022,530 B2 | 7/2018 | Tekeste |
| 10,039,884 B2 | 8/2018 | Ferreri et al. |
| 10,046,155 B2 | 8/2018 | Carter et al. |
| 10,064,576 B2 | 9/2018 | Devgon et al. |
| 10,076,272 B2 | 9/2018 | Devgon et al. |
| 10,086,142 B2 | 10/2018 | Tekeste |
| 10,105,085 B2 | 10/2018 | Andreae et al. |
| 10,105,494 B2 | 10/2018 | Alheidt et al. |
| 10,112,033 B2 | 10/2018 | Burkholz et al. |
| 10,143,411 B2 | 12/2018 | Cabot |
| 10,182,753 B2 | 1/2019 | Davis et al. |
| 10,219,982 B2 | 3/2019 | Weir et al. |
| 10,232,088 B2 | 3/2019 | Burkholz et al. |
| 10,232,140 B2 | 3/2019 | McKinnon |
| 10,238,325 B2 | 3/2019 | Burkholz et al. |
| 10,238,852 B2 | 3/2019 | Burkholz et al. |
| 10,245,416 B2 | 4/2019 | Harding et al. |
| 10,272,237 B2 | 4/2019 | Stout et al. |
| 10,300,247 B2 | 5/2019 | Devgon et al. |
| 10,307,571 B2 | 6/2019 | Burkholz |
| 10,357,636 B2 | 7/2019 | Sonderegger et al. |
| 10,391,031 B2 | 8/2019 | Yevmenenko et al. |
| 10,426,929 B2 | 10/2019 | Burkholz et al. |
| 2002/0120215 A1 | 8/2002 | Crawford et al. |
| 2003/0009150 A1 | 1/2003 | Pepin |
| 2003/0083620 A1 | 5/2003 | Luther et al. |
| 2003/0225369 A1 | 12/2003 | McMichael et al. |
| 2004/0092879 A1 | 5/2004 | Kraus et al. |
| 2004/0138622 A1 | 7/2004 | Palasis |
| 2004/0181192 A1 | 9/2004 | Cuppy |
| 2005/0015048 A1 | 1/2005 | Chiu et al. |
| 2005/0090801 A1 | 4/2005 | Racz et al. |
| 2005/0096609 A1 | 5/2005 | Maginot et al. |
| 2005/0119597 A1 | 6/2005 | O'Mahony et al. |
| 2005/0165355 A1 | 7/2005 | Fitzgerald |
| 2005/0192558 A1 | 9/2005 | Bernard et al. |
| 2005/0273076 A1 | 12/2005 | Beasley et al. |
| 2006/0015068 A1 | 1/2006 | Amisar et al. |
| 2006/0100582 A1 | 5/2006 | Marianowicz et al. |
| 2006/0142694 A1 | 6/2006 | Bednarek et al. |
| 2006/0155209 A1 | 7/2006 | Miller et al. |
| 2006/0155244 A1 | 7/2006 | Popov |
| 2007/0088279 A1 | 4/2007 | Shue et al. |
| 2007/0100295 A1 | 5/2007 | Belley et al. |
| 2007/0219460 A1 | 9/2007 | Goldenberg |
| 2007/0282280 A1 | 12/2007 | Tennican |
| 2008/0033396 A1 | 2/2008 | Danek et al. |
| 2008/0045862 A1 | 2/2008 | Dalebout et al. |
| 2008/0097407 A1 | 4/2008 | Pishka |
| 2008/0287918 A1 | 11/2008 | Rosenman et al. |
| 2008/0300574 A1 | 12/2008 | Belson et al. |
| 2008/0319387 A1 | 12/2008 | Amisar et al. |
| 2009/0156963 A1 | 6/2009 | Noble et al. |
| 2009/0192496 A1 | 7/2009 | Suwito et al. |
| 2009/0209912 A1 | 8/2009 | Keyser et al. |
| 2010/0121218 A1 | 5/2010 | Mugan et al. |
| 2010/0160863 A1 | 6/2010 | Heuser |
| 2010/0210934 A1 | 8/2010 | Belson |
| 2010/0286657 A1 | 11/2010 | Heck |
| 2010/0305519 A1 | 12/2010 | McKinnon et al. |
| 2011/0015577 A1 | 1/2011 | Baney et al. |
| 2012/0016307 A1 | 1/2012 | Burkholz et al. |
| 2012/0041392 A1 | 2/2012 | Donawick |
| 2012/0046648 A1 | 2/2012 | Scheckel |
| 2012/0053523 A1 | 3/2012 | Harding |
| 2012/0109079 A1 | 5/2012 | Asleson et al. |
| 2012/0157968 A1 | 6/2012 | Eldredge et al. |
| 2012/0197200 A1 | 8/2012 | Belson |
| 2012/0277627 A1 | 11/2012 | Devgon |
| 2013/0006226 A1 | 1/2013 | Hong et al. |
| 2013/0102888 A1* | 4/2013 | Slim .................. C30B 7/10 600/424 |
| 2013/0121897 A1 | 5/2013 | Davis et al. |
| 2013/0131597 A1 | 5/2013 | Blaivas et al. |
| 2013/0281925 A1 | 10/2013 | Benscoter et al. |
| 2013/0289537 A1 | 10/2013 | Schertiger et al. |
| 2014/0012085 A1 | 1/2014 | Smith et al. |
| 2014/0107427 A1 | 4/2014 | Chow et al. |
| 2014/0107564 A1 | 4/2014 | Bullington et al. |
| 2014/0107800 A1 | 4/2014 | Flom et al. |
| 2014/0171803 A1 | 6/2014 | Van Hoven et al. |
| 2014/0180127 A1 | 6/2014 | Meyer et al. |
| 2014/0188002 A1 | 7/2014 | Close et al. |
| 2014/0188003 A1 | 7/2014 | Belson |
| 2014/0194833 A1 | 7/2014 | Andrus |
| 2014/0296745 A1 | 10/2014 | Cash |
| 2014/0358120 A1 | 12/2014 | Haarala et al. |
| 2014/0378867 A1 | 12/2014 | Belson |
| 2015/0005669 A1 | 1/2015 | Burkholz |
| 2015/0038909 A1 | 2/2015 | Christensen et al. |
| 2015/0065952 A1 | 3/2015 | Pacheco et al. |
| 2015/0079144 A1 | 3/2015 | Hoang et al. |
| 2015/0119859 A1 | 4/2015 | Cajamarca et al. |
| 2015/0119863 A1 | 4/2015 | Christensen et al. |
| 2015/0123398 A1 | 5/2015 | Sanders et al. |
| 2015/0148747 A1 | 5/2015 | Whitley |
| 2015/0208973 A1 | 7/2015 | Burkholz |
| 2015/0209113 A1 | 7/2015 | Burkholz et al. |
| 2015/0209510 A1 | 7/2015 | Burkholz et al. |
| 2015/0297456 A1 | 10/2015 | Marici et al. |
| 2015/0305981 A1 | 10/2015 | Cederschiöld |
| 2015/0306345 A1 | 10/2015 | Burkholz et al. |
| 2015/0313526 A1 | 11/2015 | Van Wieren |
| 2015/0320937 A1 | 11/2015 | Kosinski et al. |
| 2015/0360005 A1 | 12/2015 | Arellano et al. |
| 2016/0008517 A1 | 1/2016 | Burkholz et al. |
| 2016/0015945 A1 | 1/2016 | Warring et al. |
| 2016/0024549 A1 | 1/2016 | Yeh |
| 2016/0038067 A1 | 2/2016 | Davis et al. |
| 2016/0073937 A1 | 3/2016 | Burkholz et al. |
| 2016/0121086 A1 | 5/2016 | Castro et al. |
| 2016/0158518 A1 | 6/2016 | Hallynck et al. |
| 2016/0166772 A1 | 6/2016 | Mirzadeh et al. |
| 2016/0206858 A1 | 7/2016 | Ishida |
| 2016/0220786 A1 | 8/2016 | Mitchell et al. |
| 2016/0220790 A1 | 8/2016 | Borowicz |
| 2016/0256667 A1 | 9/2016 | Ribelin et al. |
| 2016/0325078 A1 | 11/2016 | Burkholz |

(56) References Cited

U.S. PATENT DOCUMENTS

| | | |
|---|---|---|
| 2016/0367177 A1 | 12/2016 | Edelhauser et al. |
| 2017/0043066 A1 | 2/2017 | Laub |
| 2017/0056595 A1 | 3/2017 | Alheidt et al. |
| 2017/0056639 A1 | 3/2017 | Ma |
| 2017/0119997 A1 | 5/2017 | Burkholz et al. |
| 2017/0120001 A1 | 5/2017 | Hyer et al. |
| 2017/0120008 A1 | 5/2017 | Burkholz et al. |
| 2017/0120009 A1 | 5/2017 | Garrison et al. |
| 2017/0120010 A1 | 5/2017 | Burkholz et al. |
| 2017/0120012 A1 | 5/2017 | Sonderegger et al. |
| 2017/0120013 A1 | 5/2017 | Peterson et al. |
| 2017/0120017 A1 | 5/2017 | Burkholz et al. |
| 2017/0273714 A1 | 9/2017 | Harding et al. |
| 2017/0325713 A1 | 11/2017 | Burkholz et al. |
| 2017/0333676 A1 | 11/2017 | Vincent et al. |
| 2017/0348509 A1 | 12/2017 | Burkholz et al. |
| 2017/0348511 A1 | 12/2017 | Burkholz et al. |
| 2017/0368326 A1 | 12/2017 | Burkholz et al. |
| 2018/0021543 A1 | 1/2018 | Burkholz et al. |
| 2018/0093074 A1 | 4/2018 | Burkholz et al. |
| 2018/0093085 A1 | 4/2018 | Burkholz et al. |
| 2018/0162578 A1 | 6/2018 | Ivosevic et al. |
| 2018/0272107 A1 | 9/2018 | Ehrenreich et al. |
| 2018/0280626 A1 | 10/2018 | Branson et al. |
| 2018/0289920 A1 | 10/2018 | Harding et al. |
| 2018/0289921 A1 | 10/2018 | Burkholz |
| 2018/0289922 A1 | 10/2018 | Burkholz |
| 2018/0318557 A1 | 11/2018 | Burkholz et al. |
| 2018/0353729 A1 | 12/2018 | Hu et al. |
| 2019/0021640 A1 | 1/2019 | Burkholz et al. |
| 2019/0022324 A1 | 1/2019 | Tekeste |
| 2019/0022357 A1 | 1/2019 | Burkholz et al. |
| 2019/0022367 A1 | 1/2019 | Burkholz et al. |
| 2019/0054270 A1 | 2/2019 | Bornhoft |
| 2019/0091462 A1 | 3/2019 | Bihlmaier et al. |
| 2019/0105464 A1 | 4/2019 | Naidu et al. |
| 2019/0167855 A1 | 6/2019 | Burkholz et al. |
| 2019/0167951 A1 | 6/2019 | Harding et al. |
| 2019/0167966 A1 | 6/2019 | Burkholz et al. |
| 2019/0175088 A1 | 6/2019 | Burkholz et al. |
| 2019/0209726 A1 | 7/2019 | Ma et al. |
| 2019/0209812 A1 | 7/2019 | Burkholz et al. |
| 2019/0231985 A1 | 8/2019 | Mahmoodian |
| 2019/0234540 A1 | 8/2019 | Marici et al. |
| 2019/0247642 A1 | 8/2019 | Karthikeyan et al. |
| 2019/0269889 A1 | 9/2019 | Ma et al. |

FOREIGN PATENT DOCUMENTS

| | | |
|---|---|---|
| EP | 2504054 B1 | 9/2013 |
| JP | S55119739 U | 8/1980 |
| JP | 2007029732 A | 8/2007 |
| RU | 2271835 C2 | 3/2006 |
| WO | 1996021393 A1 | 7/1996 |
| WO | 1998039054 A1 | 9/1998 |
| WO | 1999016496 A1 | 4/1999 |
| WO | 2000041617 A1 | 7/2000 |
| WO | 2000049939 A1 | 8/2000 |
| WO | 2004089437 A1 | 10/2004 |
| WO | 2006065949 A1 | 6/2006 |
| WO | 2006090637 A1 | 8/2006 |
| WO | 2006126002 A1 | 11/2006 |
| WO | 2008097949 A1 | 8/2008 |
| WO | 2008130077 A1 | 10/2008 |
| WO | 2008138351 A1 | 11/2008 |
| WO | 2009029216 A1 | 3/2009 |
| WO | 2009152470 A1 | 12/2009 |
| WO | 2010065901 A1 | 6/2010 |
| WO | 2010089154 A1 | 8/2010 |
| WO | 2010107949 A1 | 9/2010 |
| WO | 2011011436 A2 | 1/2011 |
| WO | 2011030282 A1 | 3/2011 |
| WO | 2014093472 A1 | 6/2011 |
| WO | 2012064786 A1 | 5/2012 |
| WO | 2013174381 A1 | 11/2013 |
| WO | 2016089871 A1 | 6/2016 |
| WO | 2016178974 A1 | 11/2016 |
| WO | 2017074674 A1 | 5/2017 |
| WO | 2018175529 A1 | 9/2018 |

OTHER PUBLICATIONS

Office Action for U.S. Appl. No. 13/758,585, mailed Jun. 10, 2015, 20 pgs.

Office Action for U.S. Appl. No. 13/758,585, mailed Oct. 30, 2015, 14 pgs.

Office Action for U.S. Appl. No. 13/758,585, mailed May 16, 2016, 8 pages.

Office Action for U.S. Appl. No. 14/468,826, mailed Oct. 26, 2017, 7 pages.

Office Action for U.S. Appl. No. 15/199,290, mailed Dec. 7, 2016, 30 pgs.

Office Action for U.S. Appl. No. 15/680,952, mailed Dec. 6, 2017, 27 pages.

Office Action for U.S. Appl. No. 15/014,834, mailed May 16, 2018, 33 pages.

International Search Report and Written Opinion from International Application No. PCT/US2010/042635, mailed Feb. 25, 2011.

International Search Report and Written Opinion for International Application No. PCT/US2012/035122, mailed Feb. 14, 2014.

International Search Report and Written Opinion for International Application No. PCT/US2015/046863, mailed Dec. 21, 2015.

International Search Report and Written Opinion for International Application No. PCT/US2017/016359, mailed Jun. 26, 2017, 13 pages.

International Search Report and Written Opinion from International Application No. PCT/US2018/023479, mailed Aug. 3, 2018, 10 pages.

International Search Report and Written Opinion from International Application No. PCT/US2018/023575, mailed Aug. 8, 2018, 10 pages.

International Search Report and Written Opinion for International Application No. PCT/US2018/67631, mailed Mar. 29, 2019.

Supplementary European Search Report for European Application No. EP 12776089.0, mailed May 13, 2015, 7 pgs.

Extended European Search Report for European Application No. 17748206.4 dated Aug. 8, 2019, 9 pages.

Examination Report for AU Application No. 2015306728, mailed Jul. 16, 2019, 5 pgs.

Office Action for Chinese Patent Application No. 201280029672.2, mailed May 26, 2015, 21 pgs.

Office Action for Japanese Patent Application No. 2014-508539, mailed Feb. 26, 2016, 4 pgs.

Office Action for Japanese Patent Application No. 2014-508539, mailed Nov. 1, 2016, 6 pgs.

Office Action for Russian Patent Application No. 2013152251, mailed Feb. 24, 2016, 6 pgs.

Notice of Preliminary Rejection for Korean Patent Application No. 10-2013-7030879, mailed Feb. 6, 2018, 11 pages.

Office Action for Russian Patent Application No. 2017109889, mailed Oct. 16, 2018, 23 pgs.

Office Action Japanese Patent Application No. 2017-038135, dated Feb. 14, 2018, 5 pages.

"Blood Sampling Hemolysis Study for the MaxPlus™ Positive Flow Connector," Maximus Medical Products, Inc. © 2003, 1 pg.

"Connect and Protect with BD Diagnostics—Preanalytical Systems," BD Vacutainer®, Luer-Lok™, Access Device, 2 pgs, 2006.

Cox, et al. "Blood Samples Drawn from IV Catheters Have Less Hemolysis When 5-mL (vs 10-mL) Collection Tubes are Used," J Emerg Nurs. Dec. 2004;30(6):529-33. [retrieved on Mar. 16, 2011] Retrieved from the Internet <URL: http://www.jenonline.org/article/S0099-1767(04)00634-8/fulltext>, 2 pgs.

"Evidence-Based Practice (EBP) Guideline Drawing Labs from Peripheral IV Sites," Nursing Research Council of United Hospital—Developed Apr. 2004; Revised Mar. 2009, 3 pgs.

(56) References Cited

OTHER PUBLICATIONS

Frey, "Drawing Blood Samples From Vascular Access Devices: Evidence-based Practice," Journal of Infusion Nursing: Sep./Oct. 2003, vol. 26, Issue 5, pp. 285-293, Article: CE, Abstract, [retrieved on Mar. 16, 2011], 1 pg.

Himberger Jr., "Accuracy of drawing blood through infusing intravenous lines," 2001 [retrieved on Mar. 16, 2011] Retrieved from the Internet <URL: http://www.ncbi.nlm.nih.gov/pubmed/?term=Accuracy%20of%20drawing%20blood%20through%20infusing%20intravenous%20lines>.

Jagger, et al., "Drawing Venous Blood With Syringes: A Risky Use of Injection Equipment," Advances in Exposure Prevention, vol. 5, No. 3, 2000, 3 pgs.

"Needleless IV Access Devices," BD Q-Syte™, Luer Access Split-Septum, 2007, 1 pg.

"Vascular Access Procedures," Vascular Access Procedures, [retrieved on Mar. 16, 2011] Retrieved from the Internet <URL: http://www.radiologyinfo.org/en/info.cfm?pg=vasc_access> 7 pgs.

Velano Vascular, "Introducing PIVO" [Retrieved from the Internet] <URL: http://velanovascular.com/solutions/>, 2017.

WHO guidelines on drawing blood: best practices in phlebotomy, © World Health Organization 2010, 125 pgs.

Office Action for U.S. Appl. No. 16/806,949, mailed Apr. 24, 2020, 7 pgs.

International Search Report and Written Opinion for International Application No. PCT/US2019/053581, mailed Jan. 20, 2020, 18 pgs.

Office Action for JP Application No. 2014-508539, mailed Feb. 26, 2016, 8 pgs.

Office Action for JP Application No. 2014-508539, mailed Nov. 1, 2016, 11 pgs.

Office Action for RU Application No. 2013152251, mailed Feb. 24, 2016, 14 pgs.

Office Action for JP Application No. 2017-038135, mailed Feb. 14, 2018, 9 pgs.

Office Action for JP Application No. 2019-090357, mailed Mar. 18, 2020, 12 pgs.

\* cited by examiner

SYSTEMS AND METHODS FOR CONTROLLING CATHETER DEVICE SIZE

CROSS-REFERENCE TO RELATED APPLICATIONS

This application is a continuation of U.S. patent application Ser. No. 17/735,610 entitled "Systems and Methods for Controlling Catheter Device Size", filed May 3, 2022, which is a continuation of U.S. patent application Ser. No. 17/019,763 entitled "Systems and Methods for Controlling Catheter Device Size", filed Sep. 14, 2020 (now U.S. Pat. No. 11,351,340), which is a continuation of U.S. patent application Ser. No. 15/927,506 entitled, "Systems and Methods for Controlling Catheter Device Size", filed Mar. 21, 2018 (now U.S. Pat. No. 10,773,056), which claims priority to and the benefit of U.S. Provisional Patent Application Ser. No. 62/474,203 entitled, "Systems and Methods for Controlling Catheter Device Size", filed Mar. 21, 2017, the disclosures of each of which are incorporated herein by reference in their entirety.

BACKGROUND

The embodiments described herein relate generally to catheter devices. More particularly, the embodiments described herein relate to catheter devices having a controlled size and/or catheter length.

Many medical procedures and/or surgical interventions include inserting an access device or fluid transfer device into a portion of the body. For example, catheters and/or other lumen-defining devices can be inserted into and/or through vascular structures to access portions of the body. In other instances, catheter and/or other lumen-defining devices can be used to transfer fluids from or to a patient.

In some instances, access devices and/or the like can have relatively long catheter lengths, which can present challenges during use. For example, in some instances, catheters and/or access devices used in interventional cardiology can have a length of 300 centimeters (cm) or more. In such instances, the use of such catheter and/or access devices can be cumbersome and/or difficult. In addition, the length of such catheter and/or access devices can result in undesirable bending, flexing, and/or kinking.

In other instances, fluid transfer devices and/or the like can use catheters and/or other lumen-defining devices to transfer fluids to or from a patient. In some instances, it may be desirable to maintain a relatively small and/or compact form factor of such fluid transfer devices to increase ease of use and/or decrease manufacturing and/or material costs. In some such instances, however, maintaining a relatively small and/or compact form factor can result in an undesirable reduction in an effective length and/or "reach" of a catheter included in the device.

By way of example, peripheral intravenous catheters or lines (PIVs) can be inserted into a patient and used for infusing fluids and medications. In general, PIVs are not designed for blood extraction with failure rates that typically increase with indwelling times (e.g., due to obstructions, build up, debris, clots, fibrin, etc.). In some instances, however, a fluid transfer device can be coupled to a proximal portion of a PIV (e.g., the portion outside of the body) and can be used to advance a catheter through the indwelling PIV to a position in which a distal end of the catheter extends beyond a distal end of the indwelling PIV. While such devices can position the distal end of the catheter in a portion of the vein receiving a flow of blood which may otherwise be obstructed or limited due to the presence of the indwelling PIV, some such devices can have a relatively long length in order to allow for the desired placement of the catheter beyond the PIV.

Thus, a need exists for catheter devices have a controllable size and/or catheter length.

SUMMARY

Devices and methods for transferring fluid to or from a patient through a placed peripheral intravenous catheter using a relatively compact device are described herein. In some embodiments, an apparatus includes a catheter, a housing, and an actuator. The catheter has a proximal end portion and a distal end portion and defines a lumen extending through the proximal end portion and the distal end portion. The housing is configured to house at least a portion of the catheter. The housing has a first port configured to receive the proximal end portion of the catheter and a second port configured to couple the housing to an indwelling vascular access device. The actuator is movably coupled to the housing. A portion of the actuator is disposed within the housing and is configured to be movably coupled to a portion of the catheter. The actuator is configured to be moved a first distance relative to the housing to move the distal end portion of the catheter a second distance greater than the first distance from a first position to a second position. The distal end portion of the catheter is disposed within the housing when in the first position and extends through the second port such that the distal end portion of the catheter is distal to the indwelling vascular access device when in the second position and the second port is coupled to the indwelling vascular access device.

DETAILED DESCRIPTION

Figure 1:
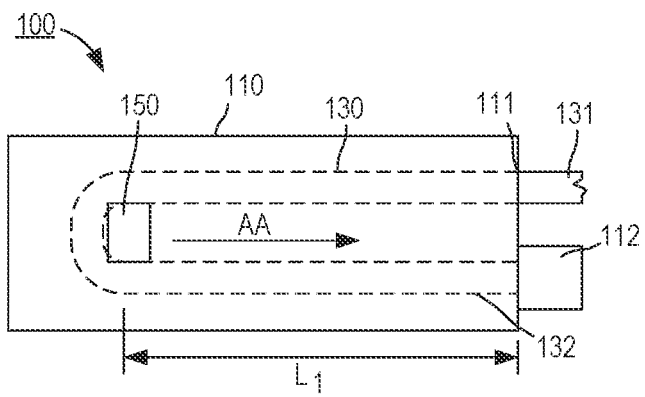
FIGS. 1 and 2 are schematic illustrations of a catheter device in a first configuration and a second configuration, respectively, according to an embodiment.

The embodiments described herein can be used in any suitable medical procedure and/or surgical intervention. For example, in some embodiments, a device such as those described herein can be used as an access device or the like during surgical intervention. In other embodiments, a device such as those described herein can be used to transfer fluids between a patient and any external connection, fluid source, fluid reservoir, etc. As one example, any of the embodiments described herein can be used, for example, to transfer fluids to or from a patient via an indwelling peripheral intravenous line (PIV) (or other suitable access device or port). In such embodiments, the device can be coupled to an indwelling or placed PIV and can be manipulated to advance a catheter through the PIV to position a distal end portion of the catheter beyond a distal end of the PIV (e.g., within a target vein). In some embodiments, the devices can have a relatively compact form factor yet are arranged such that the compact form factor does not limit and/or reduce a length, "reach," or "throw" of the catheter, as described in further detail herein.

While described herein as being used, for example, to aspirate a volume of bodily fluid (e.g., blood) from a patient, it should be understood that the embodiments and/or devices are not limited thereto. For example, in some instances, the embodiments and/or devices can be used to aspirate bodily fluid including but not limited to, blood, cerebrospinal fluid, urine, bile, lymph, saliva, synovial fluid, serous fluid, pleural fluid, amniotic fluid, mucus, vitreous, air, and the like, or any combination thereof. In other instances, the embodiments and/or devices can be used to deliver one or more fluids from a fluid source to the patient. In still other instances, the embodiments and/or devices can be used in any suitable procedure or the like involving catheterization of a target region in the body. That is to say, the embodiments and/or devices are not limited to transferring fluids to or from a patient and can be used, for example, to provide access to a target region in the body for any suitable purpose. While at least some of the devices are described herein as being used with and/or coupled to a PIV in order to transfer fluid to or from a patient, it should be understood that such use is presented by way of example only and not limitation. In other instances, for example, any of the devices described herein can be coupled to and/or otherwise used with any suitable access device such as a needle, a peripherally inserted central catheter (PICC), and/or any other lumen-containing device. Moreover, it should be understood that references to "a patient" need not be limited to a human patient. For example, any of the devices described herein can be used in any suitable procedure performed on an animal (e.g., by a veterinarian and/or the like).

In some embodiments, an apparatus includes a catheter, a housing, and an actuator. The catheter has a proximal end portion and a distal end portion and defines a lumen extending through the proximal end portion and the distal end portion. The housing is configured to house at least a portion of the catheter. The housing has a first port configured to receive the proximal end portion of the catheter and a second port configured to couple the housing to an indwelling vascular access device. The actuator is movably coupled to the housing. A portion of the actuator is disposed within the housing and is configured to be movably coupled to a portion of the catheter. The actuator is configured to be moved a first distance relative to the housing to move the distal end portion of the catheter a second distance greater than the first distance from a first position to a second position. The distal end portion of the catheter is disposed within the housing when in the first position and extends through the second port such that the distal end portion of the catheter is distal to the indwelling vascular access device when in the second position and the second port is coupled to the indwelling vascular access device.

In some embodiments, an apparatus includes a catheter, a housing, and an actuator. The catheter has a proximal end portion and a distal end portion and defines a lumen extending through the proximal end portion and the distal end portion. The housing is configured to house at least a portion of the catheter. The housing having a first port configured to receive the proximal end portion of the catheter and a second port configured to couple the housing to an indwelling peripheral intravenous line. The actuator is coupled to the housing and is configured to be moved along a predetermined length of the housing. A portion of the actuator is disposed within the housing and is configured to movably receive a portion of the catheter. The actuator is configured to be moved along the predetermined length of the housing to move the distal end portion of the catheter between a first position, in which the distal end portion of the catheter is disposed within the housing, and a second position, in which the distal end portion of the catheter extends through the second port such that the distal end portion of the catheter is distal to the second port. The distal end portion of the catheter is moved a distance greater than the predetermined length of the housing when moved between the first position and the second position.

In some embodiments, a method includes coupling a port of a fluid transfer device to a peripheral intravenous line at least partially disposed within a vein of a patient. The fluid transfer device includes a housing having the port, a catheter movably disposed in the housing, and an actuator movably coupled to the housing. A portion of the actuator is disposed within the housing and is configured to movably receive a portion of the catheter. The actuator is moved a first distance relative to the housing, where the first distance is less than a length of the housing. The distal end portion of the catheter is moved a second distance relative to the housing as a result of moving the actuator the first distance, where the second distance is greater than a length of the housing. Moving the distal end portion of the catheter is such that the distal end portion of the catheter is moved from a first position, in which the distal end portion of the catheter is disposed in the housing, to a second position, in which the distal end portion of the catheter is distal to the port.

In some embodiments, an apparatus includes a housing, a catheter at least partially disposed in the housing, and an actuator. The housing has a first port that fixedly receives a proximal end portion of the catheter, and a second port configured to couple the housing to an access device in fluid communication with a patient. The actuator is movably coupled to the housing and is configured to movably receive a portion of the catheter. The actuator is configured to be moved a first distance relative to the housing to move the distal end portion of the catheter a second distance greater than the first distance. The distal end portion of the catheter being moved between a first position within the housing to a second position in which a portion of the catheter extends through the second port such that the distal end portion of the catheter is within the patient and distal to the access device.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "catheter" and "cannula" are used interchangeably to describe an element configured to define a passageway for accessing a portion of the body (e.g., of a human and/or animal). In some instances, the passageway defined by a catheter and/or cannula can be used for moving a bodily fluid or physical object (e.g., a stent, a punctate plug, a hyaluronic-acid-gel, etc.) from a first location to a second location. While cannulas can be configured to receive a trocar, a guide wire, or an introducer to deliver the cannula to a volume inside the body of a patient, the cannulas referred to herein need not include or receive a trocar, guide wire, or introducer.

As used herein, the words "proximal" and "distal" refer to the direction closer to and away from, respectively, a user who would place the device into contact with a patient.

Thus, for example, the end of a device first touching the body of the patient would be the distal end, while the opposite end of the device (e.g., the end of the device being manipulated by the user) would be the proximal end of the device.

The embodiments described herein and/or portions thereof can be formed or constructed of one or more biocompatible materials. In some embodiments, the biocompatible materials can be selected based on one or more properties of the constituent material such as, for example, stiffness, toughness, durometer, bioreactivity, etc. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes, and/or blends and copolymers thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof.

Figure 2:
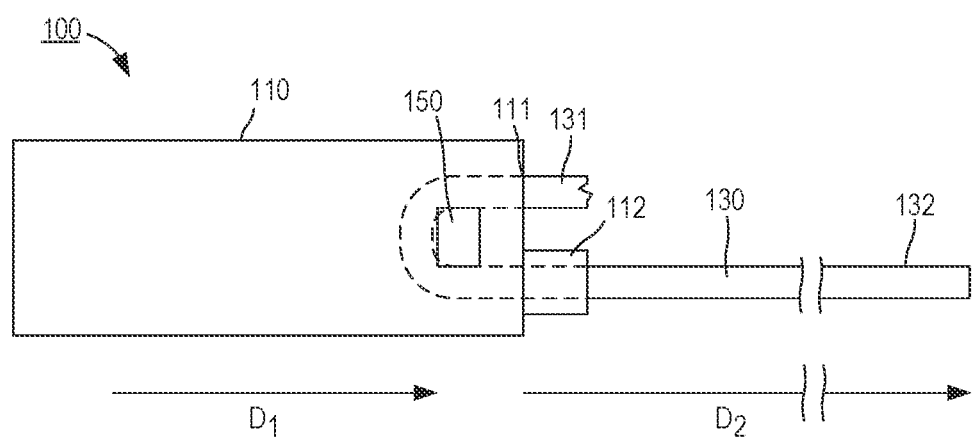

FIGS. 1 and 2 are schematic illustrations of a catheter device 100 in a first configuration and second configuration, respectively, according to an embodiment. In some embodiments, the catheter device 100 (also referred to herein as "device") can be configured to couple to and/or otherwise engage an access device and/or the like and manipulated to place a portion of a catheter in a desired position within the body. For example, the device 100 can be coupled to an indwelling peripheral intravenous catheter (PIV) to transfer bodily fluid from and/or transfer fluid to a portion of a patient (e.g., aspirate a volume of blood or infuse a drug or substance), as described in further detail herein.

The device 100 can be any suitable shape, size, and/or configuration. As shown in FIG. 1, the device 100 includes at least a housing 110, a catheter 130 (or cannula), and an actuator 150. The housing 110 can be any suitable configuration. For example, in some embodiments, the housing 110 can be an elongate member having a substantially circular cross-sectional shape. In some embodiments, the shape of the housing 110 and/or one or more features and/or surface finishes of at least an outer surface of the housing 110 can be arranged to increase the ergonomics of the device 100, which in some instances, can allow a user to manipulate the device 100 with one hand (i.e., single-handed use). As described in further detail herein, the arrangement of the device 100 is such that the housing 110 has a relatively compact length or the like without limiting and/or reducing a length of the catheter 130.

The housing 110 has a first port 111 and a second port 112. The first port 111 is configured to fixedly receive a proximal end portion 131 of the catheter 130 and the second port is configured to movably receive a distal end portion 132 of the catheter 130. While the first port 111 and the second port 112 are shown in FIG. 1 as being disposed on the same side of the housing 110 (e.g., a distal side and/or along a distal surface), in other embodiments, a housing can include a first port and a second port disposed at any suitable position along the housing (e.g., the ports can be disposed along the same surface or along different surfaces).

The ports 111 and 112 can be any suitable configuration. For example, in some embodiments, the first port 111 can be a clamp, grommet, O-ring, compression member, Luer Lok™, and/or any other suitable coupler. In this manner, the first port 111 can receive the proximal end portion 131 of the catheter 130 to allow a portion of the catheter 130 to be disposed within the housing 110 while maintaining a fixed portion (e.g., the proximal end portion 131) of the catheter 130 outside of the housing 110, as described in further detail herein. In some embodiments, the second port 112 can be a lock mechanism and/or coupler configured to couple the housing 110 to a PIV (e.g., an indwelling PIV) and/or any suitable adapter coupled to a PIV (e.g., an IV extension set or the like). For example, in some embodiments, the second port 112 can be a Luer Lok™, a "Clip-Lock-Snap" connection, and/or the like configured to physically and fluidically couple to, for example, the PIV. Moreover, the second port 112 is configured to movably receive the distal end portion 132 of the catheter 130 to allow the distal end portion 132 of the catheter 130 to be advanced through the second port 112 and the PIV (not shown in FIGS. 1 and 2) to be at least partially disposed within a vein of a patient (e.g., the vein in which the PIV is dwelling), as described in further detail herein.

The catheter 130 includes the proximal end portion 131 and the distal end portion 132 and defines a lumen (not shown) that extends through the proximal end portion 131 and the distal end portion 132. While described as defining a lumen, in some embodiments, the catheter 130 can include and/or define multiple lumens, channels, flow paths, etc. Although not shown in FIGS. 1 and 2, the proximal end portion 131 of the catheter 130 can include and/or can be coupled to a coupler and/or lock configured to physically and fluidically couple the catheter 130 to any suitable device and/or reservoir (e.g., a syringe, fluid reservoir, sample reservoir, evacuated container, fluid source, etc.). The distal end portion 132 of the catheter 130 is configured to be inserted into a portion of a patient's body, as described in further detail herein.

At least a portion of the catheter 130 is movably disposed within the housing 110. In some embodiments, the catheter 130 can be moved (e.g., via movement of the actuator 150) between a first position and a second position to transition the device 100 between the first configuration and the second configuration, respectively. More specifically, the distal end portion 132 of the catheter 130 is disposed within the housing 110 when the catheter 130 is in the first position (FIG. 1) and at least a portion of the catheter 130 extends through the second port 112 and the PIV (not shown) to place a distal end of the catheter 130 in a distal position relative to the PIV when the catheter 130 is in the second position (FIG. 2), as described in further detail herein.

The catheter 130 can be formed from any suitable material or combination of materials, which in turn, can result in the catheter 130 having any suitable stiffness or durometer. In some embodiments, at least a portion of the catheter 130 can be formed of a braided material or the like, which can change, modify, and/or alter a flexibility of the catheter 130 in response to a bending force or the like. In some embodiments, forming the catheter 130 of the braided material or the like can reduce a likelihood of kinking and/or otherwise deforming in an undesired manner. In addition, forming at least a portion of the catheter 130 of a braided material can result in a compression and/or deformation in response to a compression force exerted in a direction of a longitudinal centerline defined by the catheter 130 (e.g., an axial force or the like). In this manner, the catheter 130 can absorb a portion of force associated with, for example, impacting an obstruction or the like.

The catheter 130 can be any suitable shape, size, and/or configuration. For example, in some embodiments, at least a portion of the catheter 130 can have an outer diameter (e.g., between 8 french and 18 french, between 8-gauge and 33-gauge, and/or any other suitable size or range of sizes) that is substantially similar to or slightly smaller than an inner diameter defined by a portion of the second port 112 and/or an inner diameter defined by a portion of the PIV. In this manner, an inner surface of the second port 112 and/or PIV can guide the catheter 130 as the catheter 130 is moved therethrough, as described in further detail herein. In some embodiments, such an arrangement can limit and/or can substantially prevent bending, deforming, and/or kinking of a portion of the catheter 130 during use.

In some embodiments, the catheter 130 can have a length sufficient to place a distal surface of the catheter 130 in a desired position relative to a distal surface of the PIV when the catheter 130 is in the second position. In other words, the length of the catheter 130 can be sufficient to define a predetermined and/or desired distance between the distal surface of the catheter 130 and the distal surface of the PIV when the catheter 130 is in the second position. In some instances, placing the distal surface of the catheter 130 at the predetermined and/or desired distance from the distal surface of the PIV can, for example, place the distal surface of the catheter 130 in a desired position within a vein, as described in further detail herein.

In some embodiments, the length of the catheter 130 can be greater than a length of the housing 110. Moreover, a length of a portion of the catheter 130 disposed in the housing 110 can be greater than the length of the housing 110. In the embodiment shown in FIGS. 1 and 2, for example, the portion of the catheter 130 disposed in the housing 110 can form and/or can be arranged in a U-shaped configuration. That is to say, the catheter 130 can form a U-bend or 180° turn in the housing 110. The portion of the catheter 130 disposed in the housing 110 can be mirrored about a centerline of the U-bend or the like. Thus, the arrangement of the catheter 130 substantially doubles a length $L_1$ of the catheter 130 disposed in the housing 110 when compared to a length of a catheter having a straight or non-bent configuration.

In some embodiments, the doubling of the length $L_1$ of the catheter 130 disposed in the housing 110 can result in a similar doubling (or substantial doubling) of a "reach" of the catheter 130 for a given length of the housing 110. In other embodiments, the doubling of the length $L_1$ of the catheter 130 disposed in the housing 110 can allow a length of the housing 110 to be reduced without a similar or corresponding reduction in the length or reach of the catheter 130, as described in further detail herein. Moreover, arranging the catheter 130 in a U-shaped configuration within the housing 110 can result in a shorter unsupported portion of the catheter 130 when compared to an unsupported portion of a catheter having a straight or non-bent configuration. As described in further detail herein, such an arrangement can, for example, reduce a likelihood of undesired bowing, kinking, bending, deflecting, and/or deforming, as the catheter 130 is advanced to the second position.

The actuator 150 of the device 100 can be any suitable shape, size, and/or configuration. The actuator 150 is movably coupled to the housing 110 and the catheter 130. More specifically, the actuator 150 can include a first portion disposed outside of the housing 110 and a second portion disposed within the housing 110. In this manner, a user can engage the first portion to move the actuator 150 relative to the housing 110, as indicated by the arrow AA in FIG. 1. In some embodiments, the housing 110 can define a range of motion of the actuator 150. For example, in some embodiments, a portion of the actuator 150 (e.g., coupling the first portion to the second portion) can extend through a slot defined by the housing 110. In such embodiments, a length of the slot can define an axial range of motion for the actuator 150. That is to say, the actuator 150 can move within the slot along a length of the housing 110.

Although not shown in FIGS. 1 and 2, the second portion of the actuator 150 is movably coupled to the catheter 130. For example, in some embodiments, the second portion of the actuator 150 can be a relatively rigid sleeve or the like that defines a lumen configured to movably receive a portion of the catheter 130. In some embodiments, the second portion (e.g., sleeve) can form a U-shape or the like such that a portion of the catheter 130 disposed within the second portion of the actuator 150 likewise forms a U-shape (as described above). In other embodiments, the second portion can form a U-shaped channel or open surface (e.g., not forming an enclosed sleeve). In still other embodiments, the second portion can form any suitable shape and/or can include any suitable contoured surface. For example, in some embodiments, the second portion can be L-shaped, V-shaped, W-shaped, etc. having any suitable radius of curvature. The arrangement of the second portion and the catheter 130 is such that the catheter 130 can move substantially freely through the second portion. In other embodiments, an outer surface of the catheter 130 can contact an inner surface of the second portion of the actuator 150 such that a friction force resulting from the contact at least partially resists movement of the catheter 130 through the second portion of the actuator 150.

The arrangement of the device 100 is such that moving the actuator 150 along a length of the housing 110 advances a portion of the catheter 130 through the actuator 150, which in turn, moves the distal end portion 132 of the catheter 130 between the first position and the second position. As described above, the proximal end portion 131 of the catheter 130 is fixedly coupled to the first port 111 while the distal end portion 132 of the catheter 130 is configured to be moved relative to the housing 110 (e.g., through the second port 112). Thus, as shown in FIG. 2, moving the actuator 150 in a distal direction (e.g., the AA direction) advances a portion of the catheter 130 through the actuator 150 (e.g., the second portion of the actuator 150, not shown). In turn, the distal end portion 132 of the catheter 130 is moved from the first position (FIG. 1) to the second position (FIG. 2). By having the proximal end portion 131 of the catheter 130 fixedly coupled to the first port 111 and by arranging the catheter 130 in a U-shape within the housing 110 (as described above), moving the actuator 150 a first distance $D_1$ (FIG. 2) moves the distal end portion 132 of the catheter 130 a second distance D2 (FIG. 2) that is substantially twice the first distance $D_1$. In some instances, the second distance D2 can be sufficient to dispose a distal surface of the catheter 130 in a desired position relative to a distal surface of the PIV (not shown in FIGS. 1 and 2). In this manner, the device 100 can include the housing 110 that has a compact, limited, and/or reduced length while the catheter 130 has a length sufficient to extend a desired distance (e.g., at least partially into a PIV or at least partially through the PIV such that the distal end portion 132 of the catheter 130 is beyond or distal to a distal end of a PIV).

Figure 3:
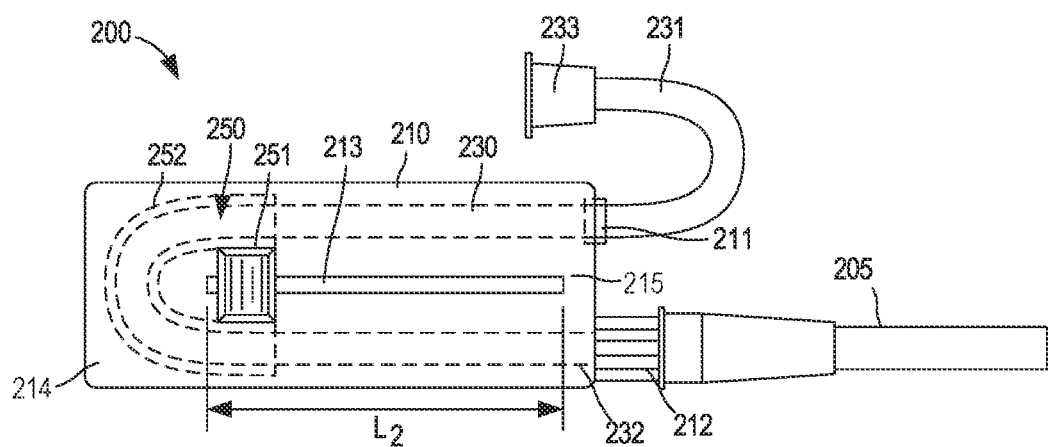
FIGS. 3 and 4 are schematic illustrations of a catheter device in a first configuration and a second configuration, respectively, according to an embodiment.
Figure 4:
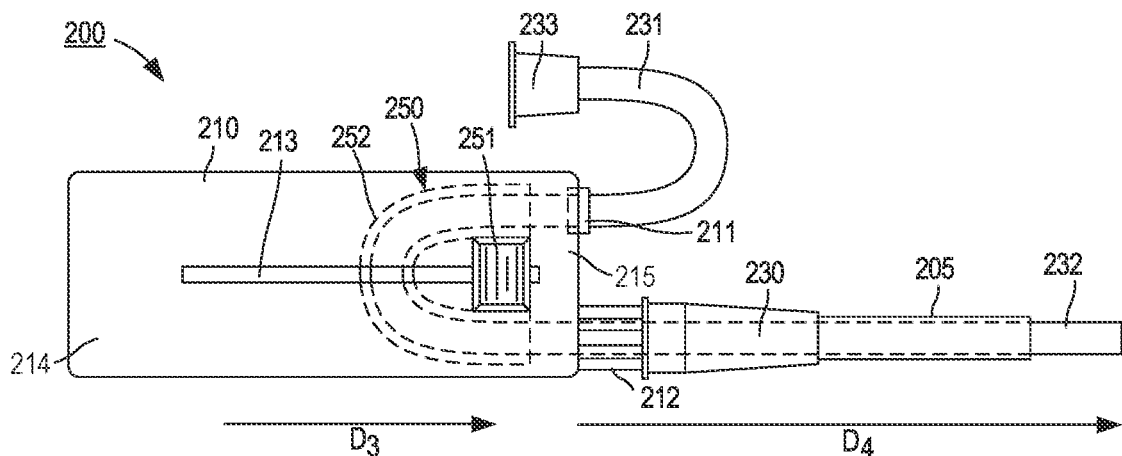

FIGS. 3 and 4 are schematic illustrations of a catheter device 200 in a first configuration and second configuration, respectively, according to an embodiment. In some embodiments, the catheter device 200 (also referred to herein as "device") can be configured to couple to and/or otherwise engage an access device and/or the like and manipulated to place a portion of a catheter in a desired position within the body. For example, the device 200 can be coupled to an indwelling peripheral intravenous catheter (PIV) 205 to transfer bodily fluid from and/or transfer fluid to a portion of a patient, as described in further detail herein.

The device 200 can be any suitable shape, size, and/or configuration. As shown in FIG. 3, the device 200 includes at least a housing 210, a catheter 230 (or cannula), and an actuator 250. The housing 210 can be any suitable configuration. For example, in some embodiments, the housing 210 can be an elongate member having a substantially circular cross-sectional shape. In some embodiments, the shape of the housing 210 and/or one or more features and/or surface finishes of at least an outer surface of the housing 210 can be arranged to increase the ergonomics of the device 200, which in some instances, can allow a user to manipulate the device 200 with one hand (i.e., single-handed use). In some embodiments, the housing 210 can be substantially similar to the housing 110 described above with reference to FIGS. 1 and 2. Thus, portions of the housing 210 are not described in further detail herein.

The housing 210 has a proximal end portion 214 and a distal end portion 215. The housing 210 includes a first port 211 and a second port 212. The ports 211 and 212 can be any suitable configuration such as those described above with reference to the first port 111 and the second port 112, respectively. In the embodiment shown in FIGS. 3 and 4, the first port 211 and the second port 212 are disposed on or along the distal end portion 215 of the housing 210. The first port 211 is configured to fixedly receive a proximal end portion 231 of the catheter 230. The second port 212 is configured to movably receive a distal end portion 232 of the catheter 230. Moreover, the second port 212 can be a lock mechanism and/or coupler configured to couple the housing 210 to the PIV 205 (e.g., an indwelling PIV), as described above.

The catheter 230 of the device 200 can be any suitable shape, size, and/or configuration. For example, in some embodiments, the catheter 230 can be substantially similar to the catheter 130 described above with reference to FIGS. 1 and 2. Thus, portions of the catheter 230 are not described in further detail herein. For example, as described above with reference to the catheter 130, in the embodiment shown in FIGS. 3 and 4, the catheter 230 can be formed from any suitable material such as those described herein. Similarly, the catheter 230 can have any suitable diameter configured to allow at least a portion of the catheter 230 to be moved through the second port 212 without undesirable bending, deforming, kinking, etc., as described above with reference to the catheter 130.

Although not shown in FIGS. 3 and 4, the catheter 230 defines a lumen that extends through the proximal end portion 231 and the distal end portion 232. The proximal end portion 231 of the catheter 230 includes and/or is coupled to a coupler 233 (e.g., a Luer Lok™™ or the like) configured to physically and fluidically couple the catheter 230 to any suitable device and/or reservoir (e.g., a syringe, fluid reservoir, sample reservoir, evacuated container, fluid source, etc.). The distal end portion 232 of the catheter 230 is configured to be inserted into a portion of a patient's body, as described in further detail herein.

At least a portion of the catheter 230 is movably disposed within the housing 210. In some embodiments, the catheter 230 can be moved (e.g., via movement of the actuator 250) between a first position, in which the distal end portion 232 of the catheter 230 is disposed within the housing 210 (FIG. 3), and a second position, in which at least a portion of the catheter 230 extends through the second port 212 and the PIV 205 to place a distal end of the catheter 230 in a distal position relative to the PIV 205 (FIG. 4), as described in further detail herein. In some embodiments, the catheter 230 can have a length sufficient to place a distal surface of the catheter 230 in a desired position relative to a distal surface of the PIV 205 when the catheter 230 is in the second position. In other words, the length of the catheter 230 can be sufficient to define a predetermined and/or desired distance between the distal surface of the catheter 230 and the distal surface of the PIV 205 when the catheter 230 is in the second position. In some instances, placing the distal surface of the catheter 230 at the predetermined and/or desired distance from the distal surface of the PIV 205 can, for example, place the distal surface of the catheter 230 in a desired position within a vein.

In some embodiments, for example, the predetermined and/or desired distance between the distal surface of the catheter 230 and the distal surface of the PIV 205 can be between about 0.0 millimeters (mm) and about 50.0 mm. In other embodiments, the predetermined and/or desired distance can be between about 15.0 mm and about 30.0 mm. In still other embodiments, the distal end portion 232 of the catheter 230 can be advanced, for example, through a hub of the PIV 205 while remaining proximal to the distal surface of the PIV 205 (e.g., the distal end portion 232 of the catheter 230 does not extend through the PIV 205). For example, in some embodiments, the predetermined and/or desired distance between the distal surface of the catheter 230 and the distal surface of the PIV 205 can be when the distal surface of the catheter 230 is between about 80.0 mm and about 0.0 mm proximal to the distal surface of the PIV 205 (e.g., −80.0 mm to about 0.0 mm).

In some embodiments, the length of the catheter 230 can be based at least in part on a desired and/or intended use. For example, in some embodiments, the device 200 can be configured for use in interventional cardiology wherein the catheter 230 can have a length of, for example, 320.0 centimeters (cm) or more. In other embodiments, the device 200 can be configured for use in fluid transfer via a PIV (as described in detail herein) and can have a length between about 1.77 cm and about 25.4 cm (about 0.5 inches (in) to about 10.0 in).

In some embodiments, the length of the catheter 230 can be greater than a length of the housing 210. Accordingly, a portion of the catheter 230 can be arranged in the housing 210 such that a length of the portion of the catheter 230 disposed therein is greater than a length of the housing 210. For example, as described in detail above with reference to the catheter 130, in the embodiment shown in FIGS. 3 and 4, the catheter 230 can be disposed in the housing 210 in a U-shaped configuration. That is to say, the catheter 230 can form a U-bend or 180° turn in the housing 210. The portion of the catheter 230 disposed in the housing 210 can be mirrored about a centerline of the U-bend or the like. Thus, the arrangement of the catheter 230 doubles a length of the catheter 230 disposed in the housing 210 without increasing a length of the housing 210, as described above with reference to the device 100 shown in FIGS. 1 and 2. Moreover, in some embodiments, the U-shaped configuration of the catheter 230 can result in a reduced portion of the catheter 230 that is unsupported within the housing 210, which in turn, can reduce a likelihood of undesired kinking, bending, bowing, deflecting, deforming, etc. of a portion of the catheter 230 as the catheter 230 is moved toward the second position. In other words, reducing an unsupported length of the catheter 230 can result in the catheter 230 being more "pushable" (e.g., able to be advanced without undesired reconfiguration) from the first position to the second position.

The actuator 250 of the device 200 can be any suitable shape, size, and/or configuration. As shown in FIGS. 3 and 4, the actuator 250 is movably coupled to the housing 210 and the catheter 230. The actuator 250 includes a first portion 251 (e.g., an engagement portion) disposed outside of the housing 210 and a second portion 252 (e.g., a sleeve portion) disposed within the housing 210. The first portion 251 of the actuator 250 can be arranged as a push button, tab, knob, slider, etc. The second portion 252 of the actuator 250 can be, for example, a relatively rigid sleeve, tube, conduit, channel, and/or the like that defines a lumen, surface, and/or path within or along which a portion of the catheter 230 can be moved. As shown in FIGS. 3 and 4, the second portion 252 is substantially U-shaped and can have any suitable radius of curvature. The lumen and/or path defined by the second portion 252 of the actuator 250 movably receives the portion of the catheter 230 such that the portion of the catheter 230 disposed within the second portion 252 of the actuator 250 likewise forms a U-shape, as shown in FIGS. 3 and 4. In some embodiments, the radius of curvature of the second portion 252 can be such that the portion of the catheter 230 can move substantially freely through the second portion 252 of the actuator 250 without kinking, bending, binding, and/or otherwise undesirably deforming. While the second portion 252 of the actuator 250 is shown and described with reference to FIGS. 3 and 4 as being U-shaped, in other embodiments, an actuator and/or a portion thereof can have any suitable shape, size, and/or configuration, as described in further detail herein.

As described above with reference to the actuator 150 shown in FIGS. 1 and 2, a user can engage the first portion 251 of the actuator 250 to move the actuator 250 (including the second portion 252 thereof) relative to the housing 210. As shown in FIGS. 3 and 4, the housing 210 defines a slot 213 configured to receive a portion of the actuator 250. The slot 213 has a length L2 extending along a surface of the housing 210. Thus, with a portion of the actuator 250 disposed within the slot 213, the slot 213 is operable to define a range of motion of the actuator 250 relative to the housing 210. For example, the actuator 250 can be moved in a substantially axial direction along the length L2 of the slot 213. Moreover, the slot 213 can be relatively thin such that lateral movement of the actuator 250 relative to the housing 210 (e.g., perpendicular to the axial motion) is limited and/or substantially prevented. Although not shown in FIGS. 3 and 4, in some embodiments, an outer surface of the housing 210 and/or a surface defining at least a portion of the slot 213 can include and/or can form a set of ribs, ridges, bumps, notches, etc. configured to be in contact with a surface of the actuator 250. In such embodiments, the surface of the actuator 250 can move along the ribs or the like as the actuator 250 is moved in the slot 213. As such, the movement can result in a haptic and/or audible output that can provide a user with an indicator or the like associated with movement of the actuator 250 and/or catheter 230. In some embodiments, the arrangement of the ribs or the like and the actuator 250 can act as a ratchet system or the like that can, for example, retain the actuator 250 (and thus, the catheter 230) in a substantially fixed position along the slot 213 in the absence of an external force being applied on the actuator 250 (e.g., a force applied by the user).

The arrangement of the device 200 is such that moving the actuator 250 (e.g., the first portion 251 and the second portion 252, collectively) along a length of the housing 210 advances a portion of the catheter 230 through the second portion 252 of the actuator 250. In turn, the distal end portion 232 of the catheter 230 is moved between the first position and the second position. As described above with reference to the device 100 shown in FIGS. 1 and 2, with the proximal end portion 231 of the catheter 230 fixedly coupled to the first port 211 and the distal end portion 232 of the catheter 230 configured to move relative to the housing 210, moving the actuator 250, for example, in a distal direction advances a portion of the catheter 230 through the second portion 252 of the actuator 250. The advancement of the catheter 230 through the second portion 252 of the actuator 250, in turn, moves the distal end portion of the catheter 230 from the first position to the second position, thereby transitioning the device 200 from the first configuration (FIG. 3) to the second configuration (FIG. 4).

As described above, the arrangement of the device 200 is such that moving the actuator 250 a first distance $D_3$ results in the distal end portion 232 of the catheter 230 being moved a second distance $D_4$ that is substantially twice the first distance $D_3$. In other words, displacement of the distal end portion 232 of the catheter 230 is approximately double the displacement of the actuator 250. In some instances, such an arrangement can be considered and/or referred to as a "length doubling" and/or "displacement doubling." When accessing a vein or the like via the PIV 205, the second distance $D_4$ can be sufficient to dispose a distal surface of the catheter 230 in a desired position relative to a distal surface of the PIV 205. For example, in some instances, at may be desirable to position the distal surface of the catheter 230 distal to the distal surface of the PIV 205. In such instances, the arrangement of the device 200 can be such that the housing 210 has a compact, limited, and/or reduced length while the catheter 230 has a length sufficient to extend beyond a distal end of the PIV 205.

While the arrangement of the actuator 250 and catheter 230 is described above as being used, for example, to double an amount displacement of the distal end portion for a given displacement of the actuator, in some embodiments, the arrangement can also reduce an amount of force associated with advancing the distal end portion 232 of the catheter 230. For example, in some embodiments, the "displacement doubling" arrangement can be such that the distal end portion 232 of the catheter 230 is advanced with approximately half the force that is applied on the actuator 250. In this manner, the "displacement doubling" arrangement can have and/or can be associated with a mechanical advantage similar to that of, for example, a block and tackle system. In some instances, reducing an amount of force associated with advancement of the catheter 230 can reduce and/or limit damage to the catheter 230 and/or other structure (e.g., a vein wall or portion of the PIV 205) that may otherwise result from the distal surface of the catheter 230 impacting an obstruction or the like.

Figure 5:
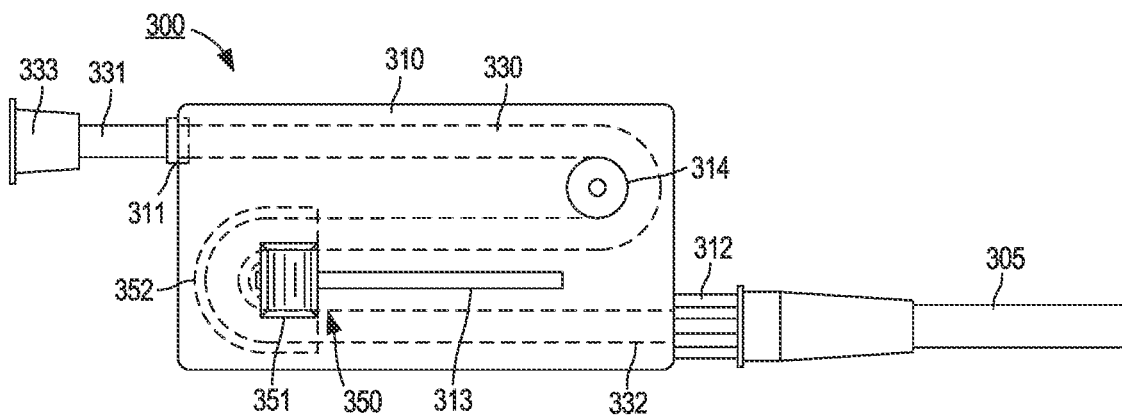
FIGS. 5 and 6 are schematic illustrations of a catheter device in a first configuration and a second configuration, respectively, according to an embodiment.
Figure 6:
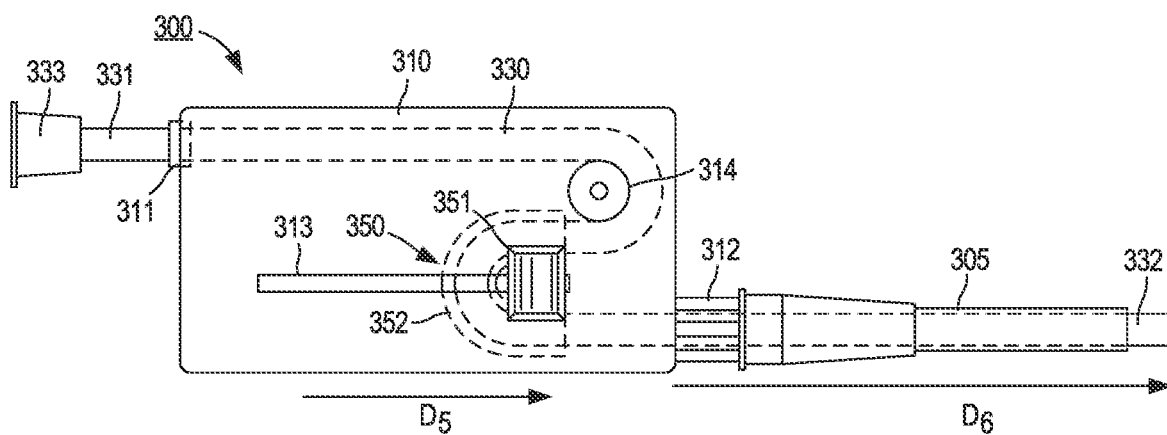

While the proximal end portion 231 and the distal end portion 232 of the catheter 230 are shown in FIGS. 3 and 4 as extending from, for example, a distal surface of the housing 210 (i.e., the same surface), in other embodiments, a device can be configured such that a proximal end portion of a catheter extends through, for example, a proximal surface of a housing and a distal end portion of the catheter extends through, for example, a distal surface of the housing. For example, FIGS. 5 and 6 are schematic illustrations of a catheter device 300 in a first configuration and second configuration, respectively, according to an embodiment. In some embodiments, the catheter device 300 (also referred to herein as "device") can be configured to couple to and/or otherwise engage an access device and/or the like and manipulated to place a portion of a catheter in a desired position within the body. For example, the device 300 can be coupled to an indwelling peripheral intravenous catheter (PIV) 305 to transfer bodily fluid from (e.g., aspiration of blood) and/or transfer fluid to (e.g., infusion of a drug or substance) a portion of a patient, as described in further detail herein.

The device 300 can be any suitable shape, size, and/or configuration. As shown in FIG. 5, the device 300 includes at least a housing 310, a catheter 330 (or cannula), and an actuator 350. In some embodiments, the device 300 can be substantially similar in form and/or function to the devices 100 and/or 200 described above with reference to FIGS. 1 and 2 and FIGS. 3 and 4, respectively. Thus, portions of the device 300 are not described in further detail herein.

The housing 310 can be any suitable configuration. For example, in some embodiments, the housing 310 can be an elongate member having a substantially circular cross-sectional shape. As described above with reference to the housings 110 and 210, in the embodiment shown in FIGS. 5 and 6, the housing 310 includes a first port 311 configured to fixedly receive a proximal end portion 331 of the catheter 330 and a second port 312 configured to movably receive a distal end portion 332 of the catheter 330. The ports 311 and 312 can be any suitable configuration. For example, in some embodiments, the first port 311 and the second port 312 can be substantially similar to the first port 111 and the second port 112, respectively, and thus, are not described in further detail herein.

The housing 310 shown in FIGS. 5 and 6 differs from the housings 110 and 210, however, by disposing and/or forming the ports 311 and 312 on opposite sides of the housing 310. For example, the first port 311, configured to fixedly couple to the proximal end portion 331 of the catheter 330, can be disposed on a proximal surface of the housing 310 and the second port 312, configured to movably receive the distal end portion 332 of the catheter 330, can be disposed on a distal surface of the housing 310. Moreover, the housing 310 can differ from the housings 110 and/or 210 by including a post 314 disposed within the housing 310. The post 314 is configured to engage a portion of the catheter 330 within the housing 310, as described in further detail herein.

The catheter 330 of the device 300 can be any suitable shape, size, and/or configuration. For example, in some embodiments, the catheter 330 can be substantially similar to the catheter 130 described above with reference to FIGS. 1 and 2. Thus, portions of the catheter 330 are not described in further detail herein. For example, as described above with reference to the catheter 130, in the embodiment shown in FIGS. 5 and 6, the catheter 330 can be formed from any suitable material such as those described herein. Similarly, the catheter 330 can have any suitable diameter configured to allow at least a portion of the catheter 330 to be moved through the second port 312 without undesirable bending, deforming, kinking, etc., as described above with reference to the catheter 130.

Although not shown in FIGS. 5 and 6, the catheter 330 defines a lumen that extends through the proximal end portion 331 and the distal end portion 332. The proximal end portion 331 of the catheter 330 includes and/or is coupled to a coupler 333 (e.g., a Luer Lok™™ or the like) configured to physically and fluidically couple the catheter 330 to any suitable device and/or reservoir (e.g., a syringe, fluid reservoir, sample reservoir, evacuated container, fluid source, etc.). As described above, the proximal end portion 331 of the catheter 330 is fixedly coupled to and/or disposed within the first port 311 disposed on or near a proximal surface of the housing 310. The distal end portion 332 of the catheter 330 is configured to be inserted into a portion of a patient's body, as described in further detail herein.

At least a portion of the catheter 330 is movably disposed within the housing 310. In some embodiments, the catheter 330 can be moved (e.g., via movement of the actuator 350) between a first position, in which the distal end portion 332 of the catheter 330 is disposed within the housing 310 (FIG. 5), and a second position, in which at least a portion of the catheter 330 extends through the second port 312 and the PIV 305 to place a distal end of the catheter 330 in a desired position relative to the PIV 305 (FIG. 6), as described in further detail herein. In some embodiments, the catheter 330 can have a length sufficient to place a distal surface of the catheter 330 in a desired position relative to a distal surface of the PIV 305 when the catheter 330 is in the second position. In other words, the length of the catheter 330 can be sufficient to define a predetermined and/or desired distance between the distal surface of the catheter 330 and the distal surface of the PIV 305 when the catheter 330 is in the second position. In some instances, placing the distal surface of the catheter 330 at the predetermined and/or desired distance from the distal surface of the PIV 305 can, for example, place the distal surface of the catheter 330 in a desired position within a vein, as described above with reference to the catheter 230.

The catheter 330 can have any suitable length such as, for example, those described above with reference to the catheter 230. In some embodiments, the length of the catheter 330 can be greater than a length of the housing 310. In some embodiments, a portion of the catheter 330 can be arranged in the housing 310 such that a length of the portion of the catheter 330 disposed therein is greater than the length of the housing 310. For example, as described in detail above with reference to the catheters 130 and 230, in the embodiment shown in FIGS. 5 and 6, the catheter 330 can be disposed in the housing 310 and can form one or more U-bends or 180° turns in the housing 310. Thus, the arrangement of the catheter 330 allows for an increase in a length of the catheter 330 disposed in the housing 310 without increasing a length of the housing 310, as described above with reference to the device 100 shown in FIGS. 1 and 2. Moreover, by forming at least one U-bend or at least one 180° turn, an effective length, reach, and/or throw of the catheter 330 can be increased without increasing a length of the housing 310. In other embodiments, such an arrangement can allow for a reduction in the length of the housing 310 without reducing the effective length, reach, and/or throw of the catheter 330, as described in further detail herein.

While described as forming one or more U-bends or 180° turns in the housing 310 in a manner substantially similar to that described above with reference to the devices 100 and 200, the device 300 can differ from the devices 100 and 200 by arranging a portion of the catheter 330 within the housing 310 in a serpentine configuration (e.g., having two or more U-bends or, for example, a W-shaped bend). For example, as shown in FIGS. 5 and 6, the housing 310 includes the post 314 configured to engage a portion of the catheter 330. More specifically, a portion of the catheter 330 can bend or wrap around the post to form a U-bend or the like with one end of the catheter 330 extending toward the first port 311 and an opposite end of the catheter 330 extending toward a portion of the actuator 350. In the embodiment shown in FIGS. 5 and 6, the post 314 can be substantially stationary or fixed and, as such, a length of a portion of the catheter 330 disposed between the first port 311 and the post 314 can similarly be fixed. As described in further detail herein, in use, the actuator 350 can be moved relative to the housing 310 and as such, can decrease or increase a length of a portion of the catheter 330 disposed between the post 314 and the portion of the actuator 350.

The actuator 350 of the device 300 can be any suitable shape, size, and/or configuration. As shown in FIGS. 5 and 6, the actuator 350 is movably coupled to the housing 310 and the catheter 330. The actuator 350 includes a first portion 351 (e.g., an engagement portion) disposed outside of the housing 310 and a second portion 352 (e.g., a sleeve portion) disposed within the housing 310. The first portion 351 of the actuator 350 can be arranged as a push button, tab, knob, slider, etc. The second portion 352 of the actuator 350 can be, for example, a relatively rigid sleeve, tube, conduit, channel, surface, and/or the like that defines a lumen or path configured to movably receive a portion of the catheter 330. As shown in FIGS. 5 and 6, the second portion 352 is substantially U-shaped and movably receives the portion of the catheter 330 such that the portion of the catheter 330 disposed therein likewise forms a U-shape, as shown in FIGS. 5 and 6. In some embodiments, the actuator 350 can be similar to and/or substantially the same as the actuator 250 and thus, is not described in further detail herein.

As described above with reference to the actuators 150 and 250, a user can engage the first portion 351 of the actuator 350 to move the actuator 350 (including the second portion 352 thereof) through, within, and/or along a slot 313 defined by the housing 310. Thus, the slot 313 defines a range of motion of the actuator 350 relative to the housing 310, as described above.

The arrangement of the device 300 is such that moving the actuator 350 (e.g., the first portion 351 and the second portion 352, collectively) along a length of the housing 310 advances a portion of the catheter 330 through the second portion 352 of the actuator 350. In turn, the distal end portion 332 of the catheter 330 is moved between the first position and the second position. More specifically, the user can exert a force on the first portion 351 of the actuator 350 to move the actuator 350 relative to the housing 310. Accordingly, the second portion 352 of the actuator 350 moves within the housing 310, which in turn, decreases or increases a distance between the second portion 352 of the actuator 350 and the post 314 of the housing 310. In other words, moving the actuator 350 relative to the housing 310 decreases or increases a length of the catheter 330 disposed between the post 314 and the second portion 352 of the actuator 350, as shown in FIG. 6. In the embodiment shown in FIGS. 5 and 6, the post 314 can form an anchor or fixation point for a portion of the catheter 330 such that the post 314 functions substantially similar to the first port 311. Thus, moving the actuator 350 in a distal direction advances a portion of the catheter 330 through the second portion 352 of the actuator 350, which in turn, moves the distal end portion 332 of the catheter 330 from the first position to the second position, as described in detail above with reference to the devices 100 and/or 200.

Moving the distal end portion 332 of the catheter 330 between the first position and the second position transitions the device 300 from the first configuration (FIG. 5) to the second configuration (FIG. 6). As described above, with the post 314 functioning in a substantially similar manner as the first port 311, the arrangement of the device 300 is such that moving the actuator 350 a first distance $D_5$ results in the distal end portion 332 of the catheter 330 being moved a second distance $D_6$ that is substantially twice the first distance $D_5$. In other words, displacement of the distal end portion 332 of the catheter 330 is approximately double the displacement of the actuator 350. In some instances, such an arrangement can be considered and/or referred to as a "length doubling" and/or "displacement doubling," described in detail above with reference to the device 200.

When accessing a vein or the like via the PIV 305, the second distance $D_6$ can be sufficient to dispose a distal surface of the catheter 330 in a desired position relative to a distal surface of the PIV 305, as described above with reference to the device 200. In this manner, the device 300 can include the housing 310 having a compact, limited, and/or reduced length while providing the catheter 330 with a length sufficient to extend beyond a distal end of a PIV 305. Moreover, by including the post 314 and arranging a portion of the catheter 330 in a serpentine configuration (e.g., forming two U-bends or the like), the first port 311 can be disposed on a proximal end portion of the housing 310 and the second port 312 can be disposed on a distal end portion of the housing 310.

While the post 314 is described above as being substantially stationary or fixed, in other embodiments, the post 314 can be formed as and/or can include a rotor or pulley configured to rotate about an axis defined by the post 314. In some embodiments, such a pulley can include and/or can act as a clutch, brake, and/or controller that can facilitate and/or resist movement of the catheter 330 relative to the post 314. Moreover, in some embodiments, the post 314 can be configured to move (e.g., independent of movement of the actuator 350) between a locked or unlocked position. For example, in some embodiments, the post 314 can be moved in a linear motion to clamp, squeeze, and/or constrain a portion of the catheter 330 between the post 314 and, for example, an inner surface of the housing 310 (e.g., a locked position). In this position, the post 314 can "lock" the catheter 330 in a fixed position. In some embodiments, the post 314 can be a coupler or the like configured to physically and/or fluidically couple two portions of the catheter 330 (e.g., couple the proximal end portion 331 to the distal end portion 332). In this manner, the catheter 330 can have a first portion with one size, shape, and/or set of characteristics and can have a second portion with a different size, shape, and/or set of characteristics.

Figure 7:
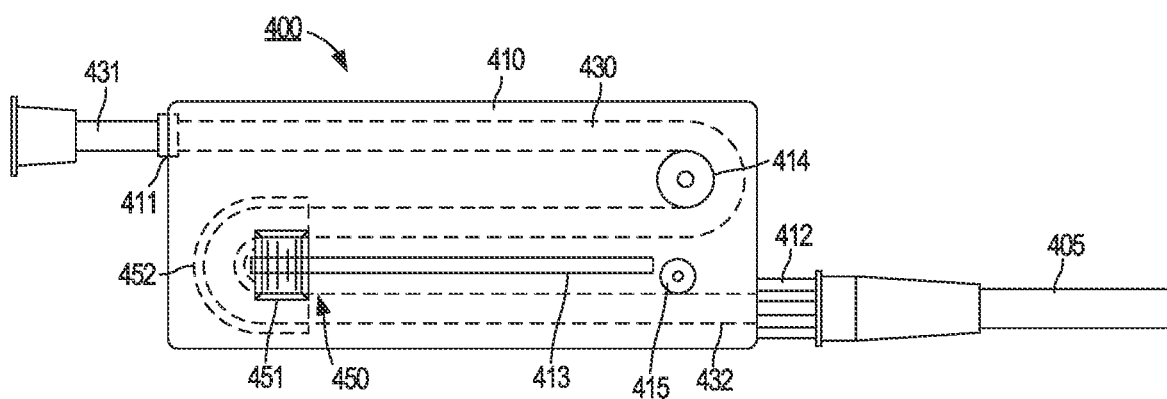
FIG. 7 is a schematic illustration of a catheter device according to an embodiment.

FIG. 7 is a schematic illustration of a catheter device 400 according to an embodiment. In some embodiments, the catheter device 400 (also referred to herein as "device") can be configured to couple to and/or otherwise engage an access device and/or the like and manipulated to place a portion of a catheter in a desired position within the body. For example, the device 400 can be coupled to an indwelling peripheral intravenous catheter (PIV) 405 to transfer bodily fluid from (e.g., aspiration of blood) and/or transfer fluid to (e.g., infusion of a drug or substance) a portion of a patient, as described in further detail herein.

The device 400 can be any suitable shape, size, and/or configuration. As shown in FIG. 7, the device 400 includes at least a housing 410, a catheter 430 (or cannula), and an actuator 450. In some embodiments, the device 400 can be substantially similar in form and/or function to the device 300 described above with reference to FIGS. 5 and 6. For example, the catheter 430 and the actuator 450 can be substantially similar in form and/or function to the catheter 330 and the actuator 350, respectively, included in the device 300. Thus, such similar portions of the device 400 are not described in further detail herein.

The housing 410 can be any suitable configuration. For example, in some embodiments, the housing 410 can be substantially similar to the housing 310 described above with reference to FIGS. 5 and 6. As such, the housing 410 includes a first port 411 configured to movably receive a proximal end portion 431 of the catheter 430 and a second port 412 configured to movably receive a distal end portion 432 of the catheter 430. The ports 411 and 412 can be any suitable configuration such as those described above with reference to the housing 310. The housing 410 also includes a post 414 disposed within the housing 410 and configured to engage a portion of the catheter 430, as described above with reference to the post 314 of the housing 310. The housing 410 shown in FIG. 7 can differ from the housing 310, however, by including a second post 415 disposed within the housing 410 and configured to engage a portion of the catheter 430 within the housing 410, as described in further detail herein.

The catheter 430 of the device 400 can be any suitable shape, size, and/or configuration. For example, in some embodiments, the catheter 430 can be substantially similar to the catheter 330 described above with reference to FIGS. 5 and 6. Thus, portions of the catheter 430 are not described in further detail herein. At least a portion of the catheter 430 is movably disposed within the housing 410. In some embodiments, the catheter 430 can be moved (e.g., via movement of the actuator 450) between a first position, in which the distal end portion 432 of the catheter 430 is disposed within the housing 410 (FIG. 7), and a second position, in which at least a portion of the catheter 430 extends through the second port 412 and the PIV 405 to place a distal end of the catheter 430 in a desired position relative to the PIV 405 (not shown), as described in detail above with reference to the device 300.

The actuator 450 of the device 400 is movably coupled to the housing 410. The actuator 450 can be any suitable shape, size, and/or configuration. For example, in some embodiments, the actuator 450 is substantially similar to the actuator 350 described above with reference to FIGS. 5 and 6. Thus, portions of the actuator are not described in further detail herein. As described above with reference to the actuator 350, a user can engage a first portion 451 of the actuator 450 to move the actuator 450 (including a second portion 452 thereof) through, within, and/or along a slot 413 defined by the housing 410. The arrangement of the device 400 is such that moving the actuator 450 (e.g., the first portion 451 and the second portion 452, collectively) along a length of the housing 410 advances a portion of the catheter 430 through, along, and/or relative to the second portion 452 of the actuator 450. In turn, the distal end portion 432 of the catheter 430 is moved between the first position and the second position, as described in detail above with reference to the device 300.

In the embodiment shown in FIG. 7, the posts 414 and 415 can be configured to rotate in response to a movement of the catheter 430. More particularly, the first post 414 can be configured to rotate in a first direction (e.g., a clockwise direction) and the second post 415 can be configured to rotate in a second direction opposite the first direction (e.g., a counterclockwise direction). In some embodiments, each of the posts 414 and 415 can be transitioned between at least a first configuration and a second configuration to selectively control movement of the catheter 430. For example, the first post 414 can be configured to rotate only in the first direction (e.g., the clockwise direction) when in the first configuration and the second post 415 can be configured to rotate only in the second direction (e.g., the counterclockwise direction) when in the first configuration. Thus, when the posts 414 and 415 are in the first configuration, the movement of the catheter 430 from the first position to the second position (e.g., in the distal direction), rotates the posts 414 and 415.

When the posts 414 and 415 are in the first configuration, however, each post 414 and 415 is substantially prevented from rotating in its associated opposite direction. For example, the first post 414 can be substantially prevented from rotating in the second direction (e.g., counterclockwise) and the second post 415 can be substantially prevented from rotating in the first direction (e.g., clockwise). In some instances, this arrangement of the posts 414 and 415 is such that movement of the catheter 430 in the proximal direction (e.g., from the second position toward the first position) is substantially prevented. In other words, by preventing rotation of the posts 414 and 415 in their opposite directions, the catheter 430 can be prevented from being moved in the proximal direction. In some embodiments, this can allow the actuator 450 to be moved in the proximal direction without a corresponding movement of the catheter 430 in the proximal direction. Thus, posts 414 and 415 and the actuator 450 can act as a ratcheting mechanism or the like that can allow the actuator 450 to be moved in the distal direction a number of times (e.g., more than one time) to move the catheter 430 in a distal direction (e.g., toward the second position). In some instances, such an arrangement can facilitate the insertion and/or advancement of relatively long catheters such as, for example, those used in interventional cardiology and/or the like.

In contrast, a user can transition the posts 414 and 415 from the first configuration to the second configuration, in which the posts 414 and 415 are configured to rotate in their associated opposite directions. For example, the first post 414 can be configured to rotate in the second direction (e.g., counterclockwise) and the second post 415 can be configured to rotate in the first direction (e.g., clockwise). In some embodiments, the posts 414 and 415 can be configured to rotate in either direction when in the second configuration. With each post 414 and 415 configured to rotate in its opposite direction, the catheter 430 can be moved in the proximal direction (e.g., from the second position toward the first position). For example, in some embodiments, the user can pull on the proximal end portion 431 of the catheter 430 to move the catheter 430 in the proximal direction. In the embodiment shown in FIG. 7, the port 411 of the housing 410 can allow for movement of the catheter 430 therethrough (e.g., in contrast to the devices 100, 200, and/or 300). Thus, when the posts 414 and 415 are in the second configuration, the catheter 430 can be retracted.

While described as being transitioned between the first configuration and the second configuration, in some embodiments, the posts 414 and 415 can be transitioned to a third configuration in which the posts 414 and 415 are locked. In other words, rotation of the posts 414 and 415 in either direction can be prevented. In this manner, the posts 414 and 415 can limit and/or substantially prevent movement of the catheter 430 in the proximal direction and the distal direction. In some embodiments, the device 400 can be in the third configuration prior to use (e.g., a storage configuration). Alternatively, the device 400 can be placed in the third configuration after use such that at least a portion of the catheter 430 is locked in a fixed position within the housing 410. In such instances, disposing, maintaining, and/or locking the portion of the catheter 430 in the housing 410 after use can reduce and/or substantially prevent undesirable fluid from exiting the catheter 430, which in turn, can reduce the spread of disease, etc.

While the devices 100, 200, 300, and 400 have been shown and/or described above as being coupled to a PIV, in other embodiments, the devices can be coupled to any suitable access device, introducer, adapter, secondary or intermediate device, etc. For example, in some instances, the second port 212 of the housing 210 of the device 200 can be coupled to an extension set or the like, which in turn, is coupled to an indwelling PIV such as those described herein. The extension set can be, for example, a dual port IV extension set such as a "Y-adapter" or "T-adapter." In this manner, the terms "Y-adapter" and "T-adapter" generally describe an overall shape of the dual port IV extension set. In other embodiments, an extension set can be a single port IV extension set. In these embodiments, the devices described herein can include a catheter having a length sufficient to extend from the housing of the device, through the extension set or other intermediate device, and through the PIV to position a distal end thereof distal to the PIV. In other embodiments, the devices 100, 200, 300 can be coupled to any suitable access device or the like and can be used for any suitable procedure, surgery, etc.

In some instances, the transfer devices described herein can be assembled during one or more manufacturing processes and packaged in a pre-assembled configuration. For example, in some instances, the assembly of the devices 200, 300, and/or 400 can be performed in a substantially sterile environment such as, for example, an ethylene oxide environment, or the like. In other embodiments, the transfer devices described herein can be packaged in a non-assembled configuration (e.g., a user can open the package and assemble the components to form the device). The components of the devices can be packaged together or separately. In some embodiments, the devices can be packaged with, for example, a PIV, an extension set, a Y-adapter or T-adapter, and/or any other suitable component.

Any of the devices described herein can be used in any suitable process, procedure, method, and/or the like. For example, in some instances, the devices described herein can be used in a medical procedure, process, and/or method for transferring fluid to or from a patient. Some such procedures can include, for example, aspirating a volume of bodily fluid from a patient via a previously placed or indwelling access device. More particularly, any of the devices described herein can be used to aspirate a volume of blood from a patient via a previously placed or indwelling peripheral intravenous line.

Figure 8:
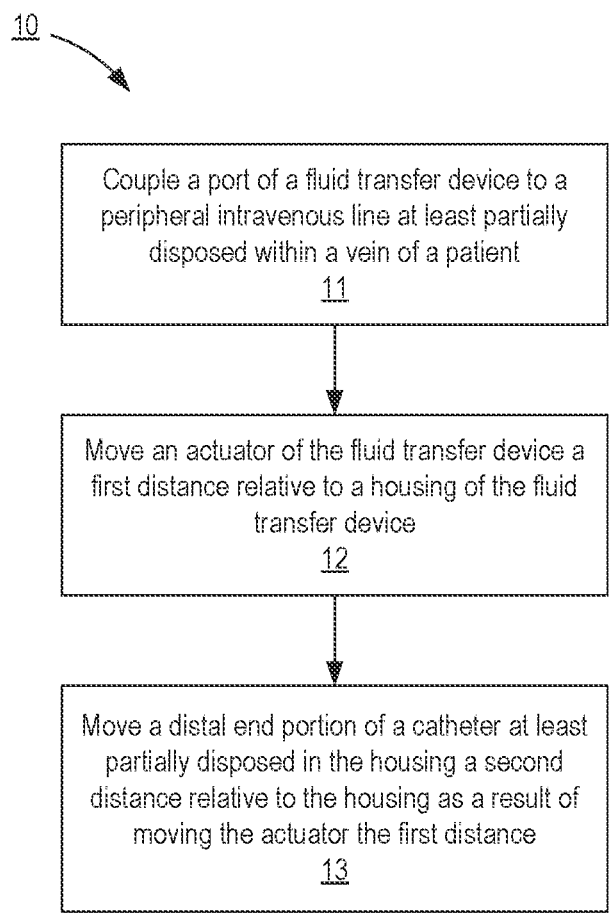
FIG. 8 is a flowchart illustrating a method of using a catheter device according to an embodiment.

For example, FIG. 8 is a flowchart illustrating a method 10 of using a fluid transfer device according to an embodiment. The fluid transfer device can be similar to or substantially the same as any of the devices 100, 200, 300, and/or 400 described in detail herein. Accordingly, the fluid transfer device can include a housing, a catheter at least partially disposed within the housing, and an actuator movably coupled to the housing. A first portion of the actuator can be disposed outside of the housing to allow a user to engage the actuator. A second portion of the actuator can be disposed within the housing and movably coupled to and/or otherwise configured to movably receive the catheter.

As shown in FIG. 8, the method 10 includes coupling the port of the fluid transfer device (or the housing) to a peripheral intravenous line (PIV) at least partially disposed within a vein of a patient, at 11. With the device coupled to the PIV (e.g., via the port), the actuator is moved a first distance relative to the housing, at 12. More particularly, the actuator can be in a first position relative to the housing (e.g., a proximal position) and can be moved the first distance to a second position relative to the housing (e.g., a distal position). In some embodiments, the actuator can be moved in response to a force exerted by the user on a portion of the actuator disposed outside of the housing. Moreover, in some embodiments, the first distance can be based on a predetermined range of motion of the actuator. For example, as described in detail above with reference to at least the devices 200, 300, and/or 400, the housing can define a slot configured to movably receive a portion of the actuator. In such embodiments, a length of the slot can define a range of motion of the actuator relative to the housing. In other words, the slot can define the first distance.

The method 10 further includes moving a distal end portion of the catheter a second distance relative to the housing as a result of moving the actuator the first distance, at 13. In other words, the arrangement of the device is such that moving the actuator the first distance, in turn, moves the distal end portion of the catheter the second distance. Moreover, as described in detail above with reference to the devices 100, 200, 300, and/or 400, the second distance is greater than the first distance. In some embodiments, moving the actuator the first distance is operable to move the distal end portion of the catheter the second distance from a first position, in which the distal end portion of the catheter is disposed in the housing, to a second position, in which the distal end portion of the catheter is distal to the port. In some instances, moving the distal end portion of the catheter the second distance places the distal end portion beyond or distal to the PIV. That is to say, the catheter can extend through the port and the PIV to place the distal end portion of the catheter in a distal position relative to the PIV. In some instances, moving the distal end portion of the catheter the second distance can place the distal end portion of the catheter in a position suitable to transfer fluid to or from the patient. For example, in some instances, a proximal end portion of the catheter can be placed in fluid communication with a fluid reservoir, syringe, and/or container configured to receive a volume of bodily fluid from the patient via the catheter after the distal end portion of the catheter has been moved the second distance, as described in detail above.

While various embodiments have been described above, it should be understood that they have been presented by way of example only, and not limitation. Where schematics and/or embodiments described above indicate certain components arranged in certain orientations or positions, the arrangement of components may be modified. Although various embodiments have been described as having particular features and/or combinations of components, other embodiments are possible having a combination of any features and/or components from any of embodiments as discussed above.

While the embodiments have been particularly shown and described, it will be understood that various changes in form and details may be made. For example, while the second portions 252, 352, and 452 of the actuators 250, 350, and 450, respectively, are shown and described above as forming a sleeve, conduit, tube, channel, etc., in other embodiments, a device can include an actuator having any suitable arrangement. For example, in some embodiments, an actuator can include a second portion that is a contoured open surface (e.g., not an enclosed tube or the like). In such embodiments, the contoured open surface can have a sickle-like shape and/or any other suitable shape. In other embodiments, an actuator can include a second portion having a pulley, bearing, pins, rollers, and/or the like configured to move in a linear direction in response to a movement of the actuator as well as to move in a rotational direction as a portion of a catheter is advanced relative to the second portion. In some instances, including an actuator with a second portion configured as a pulley or the like can facilitate movement of the catheter relative thereto. In other embodiments, the second portions 252, 352, and/or 452 of the actuators 250, 350, and/or 450, respectively, can include an inner surface having an anti-friction coating or the like configured to facilitate movement of the catheters relative thereto.

Similarly, while the second portions 252, 352, and 452 of the actuators 250, 350, and 450, respectively, are described above as being substantially U-shaped or the like, in other embodiments, an actuator can include a second portion having any suitable size, shape, and/or configuration. For example, in some embodiments, the second portion of the actuator can have a relatively small radius of curvature and can have, for example, a V-shape or the like. In other embodiments, the second portion of the actuator can have a W-shape with a center or central portion forming a clutch, brake, choke, etc. (e.g., can have an arrangement similar to the optional arrangement of the post 314 described above). In other embodiments, the second portion can have any suitable shape that allows for advancement of a portion of the catheter along or relative to the second portion.

As another example, although not shown in the devices 100, 200, 300 and/or 400, any of the housings included in the embodiments described herein can include one or more internal supports or the like configured to support the catheter within the housing. Such internal supports can be, for example, guides, tracks, rails, springs, sleeves, sponges, pads, etc. configured to selectively engage a portion of the catheter. In this manner, the internal supports can limit and/or substantially prevent undesired deformation and/or deflection of a portion of the catheter as the device is transitioned between the first configuration and the second configuration.

While described as limiting and/or substantially preventing undesired deformation and/or deflection of the catheter, in other embodiments, the catheter can be configured to deflect, bow, bend, and/or reconfigure without kinking and/or permanently deforming. For example, in some instances, a distal end surface of the catheter may impact an obstruction or the like while being advanced from the first position to the second position, which can at least temporarily obstruct and/or prevent further movement of the distal end portion of the catheter. In such instances, if a user continues to exert a force on the actuator otherwise operable to move the catheter toward the second position, an unsupported portion of the catheter within the housing can bend, flex, bow, deflect, and/or otherwise be transitioned from an "unclutched" configuration to a "clutched" configuration. In other words, a portion of the force exerted on the actuator and otherwise operable to advance the catheter toward the second position is operable to deflect, bend, flex, bow, etc. a portion of the catheter within the housing. As such, a force transmitted to and/or through the distal surface of the catheter (e.g., on the obstruction) is reduced, which in turn, can reduce damage to the catheter, an access device through which the catheter is being advanced (e.g., a PIV), a venous structure (e.g., vein wall), and/or the like.

In some embodiments, increasing or decreasing a durometer of the catheter, a length of the catheter, a length of the housing, and/or an amount of support provided, for example, by an internal support member (e.g., a guide, track, rail, spring, pad, post, etc.) can allow for a tuning or adjustment of the amount of deflection (e.g., "clutching") of the catheter and/or an amount of force transferred through the catheter. In some embodiments, a portion of the catheter can impact and/or contact an inner surface of the housing (e.g., a sidewall) when bowed, flexed, deflected, and/or clutched. In some embodiments, this arrangement can produce a visual, audible, and/or haptic indication that the distal end surface of the catheter has impacted an obstruction. In some embodiments, an internal support member (as described above) such as a pad or the like can be used to "tune" and/or alter for example, an audible and/or haptic output or indication that the distal end surface of the catheter has impacted an obstruction.

While the catheter is described above being deflected, bowed, clutched, etc. in response to impacting an obstruction, in some embodiments, the actuator can be configured to absorb and/or deflect a portion of the force otherwise used to advance the catheter toward the second position. For example, in some embodiments, an actuator such as the actuator 250 can include a suspension member, device, and/or system disposed between a first portion (e.g., the first portion 251) and a second portion (e.g., the second portion 252). Such a suspension member, device, and/or system can be a spring, a damper, a strut, a pad, etc. In some instances, for example, the first portion can be configured to move relative to the second portion in response to a force applied to the first portion when the catheter has impacted an obstruction or the like (as described above).

Although not described above with reference to specific embodiments, it should be understood that any of the embodiments described herein can be manipulated to retract a catheter from its second position to its first position. For example, in some instances, after withdrawing a desired volume of bodily fluid through the catheter 230 of the device 200, user can manipulate the device 200 by moving the actuator 250 in a proximal direction. As such, a portion of the catheter 230 is retracted through the second portion 252 of the actuator 250 as the actuator 250 is moved in the proximal direction such that a length of the catheter 230 disposed within the housing 210 is increased. In other words, a user can move the actuator 250 in a distal direction to advance the distal end portion 232 of the catheter 230 and can move the actuator in a proximal direction (i.e., an opposite direction) to retract the distal end portion 232 of the catheter into the housing 210 (e.g., after use or the like).

Any of the aspects and/or features of the embodiments shown and described herein can be modified to affect the performance of the transfer device. For example, radius of curvature of the second portion 252 of the actuator 250 can be increased or decreased to facilitate movement of the catheter 230 therethrough. In other embodiments, the length of the housing 210 can be increased or decreased to accommodate the catheter 230 having an increased or decreased length, respectively. By way of another example, any of the components of the transfer devices 100, 200, 300, and/or 400 can be formed from any suitable material that can result in a desired hardness, durometer, and/or stiffness of that component.

Where methods and/or schematics described above indicate certain events and/or flow patterns occurring in certain order, the ordering of certain events and/or flow patterns may be modified. Additionally, certain events may be performed concurrently in parallel processes when possible, as well as performed sequentially.

What is claimed:

1. An apparatus, comprising:
a catheter having a proximal end portion and a distal end portion and defining a lumen extending through the proximal end portion and the distal end portion;
a housing configured to house at least a portion of the catheter, the housing having a first port configured to receive the proximal end portion of the catheter and a second port configured to couple the housing to an indwelling vascular access device, with a post disposed within the housing; and
an actuator configured to receive a section of the catheter, the actuator configured to be moved a first distance in a distal direction along the housing to move the distal end portion of the catheter a second distance in the distal direction greater than the first distance from a first position to a second position, the distal end portion of the catheter being disposed within the housing when in the first position, the distal end portion of the catheter extending through the second port such that the distal end portion of the catheter is distal to the housing when in the second position,
wherein the catheter is engaged by the post and the actuator such that a portion of the catheter within the housing is arranged in a serpentine configuration.

2. The apparatus of claim 1, wherein the is actuator configured to be moved a first distance in the distal direction along the housing to move the distal end portion of the catheter a second distance in the distal direction greater than the first distance from the first position to the second position.

3. The apparatus of claim 2, wherein a first portion of the actuator is disposed in the housing, and wherein the housing defines a slot configured to movably receive a second portion of the actuator, the slot defining a range of motion associated with the movement of the actuator relative to the housing between a proximal position and a distal position.

4. The apparatus of claim 3, wherein the housing has a length, the length of the slot is less than the length of the housing, the distance associated with moving the distal end portion of the catheter from the first position to the second position being greater than the length of the housing.

5. The apparatus of claim 4, wherein the post is in a fixed position on the housing, and wherein moving the actuator relative to the housing decreases or increases a distance between the second portion of the actuator and the post of the housing.

6. The apparatus of claim 5, wherein moving the actuator relative to the housing decreases or increases a length of the catheter disposed between the post and the second portion of the actuator.

7. The apparatus of claim 1, wherein the post includes a rotor or pulley configured to rotate about an axis defined by the post configured to facilitate and/or resist movement of the catheter relative to the post.

8. The apparatus of claim 1, wherein the post is configured to move between locked and unlocked positions, with the post moveable in a linear motion to clamp, squeeze, and/or constrain a portion of the catheter between the post and an inner surface of the housing to lock the catheter in a fixed position.

* * * * *